(12) United States Patent
Church et al.

(10) Patent No.: US 10,202,628 B2
(45) Date of Patent: Feb. 12, 2019

(54) ASSEMBLY OF NUCLEIC ACID SEQUENCES IN EMULSIONS

(71) Applicant: President and Fellows of Harvard College, Cambridge, MA (US)

(72) Inventors: George M. Church, Brookline, MA (US); Richard C. Terry, Carlisle, MA (US); Sriram Kosuri, Cambridge, MA (US); Di Zhang, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 861 days.

(21) Appl. No.: 14/379,005

(22) PCT Filed: Feb. 14, 2013

(86) PCT No.: PCT/US2013/026045
§ 371 (c)(1),
(2) Date: Aug. 15, 2014

(87) PCT Pub. No.: WO2013/123125
PCT Pub. Date: Aug. 22, 2013

(65) Prior Publication Data
US 2015/0111256 A1    Apr. 23, 2015

Related U.S. Application Data

(60) Provisional application No. 61/600,118, filed on Feb. 17, 2012.

(51) Int. Cl.
| | | |
|---|---|---|
| *C12Q 1/68* | (2018.01) | |
| *C12P 19/34* | (2006.01) | |
| *C12N 15/10* | (2006.01) | |
| *C12Q 1/6851* | (2018.01) | |

(52) U.S. Cl.
CPC .......... *C12P 19/34* (2013.01); *C12N 15/1031* (2013.01); *C12Q 1/6851* (2013.01)

(58) Field of Classification Search
None
See application file for complete search history.

(56) References Cited

U.S. PATENT DOCUMENTS

| | | | |
|---|---|---|---|
| 8,808,986 B2 * | 8/2014 | Jacobson ........... C12N 15/1093 | |
| | | | 435/6.1 |
| 2014/0045728 A1 * | 2/2014 | Church .................. C40B 50/14 | |
| | | | 506/26 |

FOREIGN PATENT DOCUMENTS

| | | | | |
|---|---|---|---|---|
| WO | WO2010025310 | * | 3/2010 | ............. C12N 15/10 |
| WO | WO2012154201 | * | 11/2012 | ............... C12Q 1/68 |

OTHER PUBLICATIONS

Borovkov et al. High-quality gene assembly directly from unpurified mixtures of microarray-synthesized oligonucleotides. Nucleic Acids Res. Oct. 2010; 38 (19):e180 pp. 1-10. Epub Aug. 6, 2010. (Year: 2010).*
Kosuri et al. Scalable gene synthesis by selective amplification of DNA pools from high-fidelity microchips. Nat Biotechnol. Dec. 2010; 28(12):1295-9. Epub Nov. 28, 2010. (Year: 2010).*
Shendure J, Ji H. Next-generation DNA sequencing. Nat Biotechnol. Oct. 2008; 26(10):1135-45. (Year: 2008).*

* cited by examiner

*Primary Examiner* — Aaron A Priest
*Assistant Examiner* — Olayinka A Oyeyemi
(74) *Attorney, Agent, or Firm* — Banner & Witcoff, Ltd.

(57) ABSTRACT

Methods and compositions for synthesizing nucleic acid sequences in an emulsion are provided.

42 Claims, 7 Drawing Sheets
Specification includes a Sequence Listing.

SEQUENCE LISTING

<160> NUMBER OF SEQ ID NOS: 35

<210> SEQ ID NO 1
<211> LENGTH: 15
<212> TYPE: DNA
<213> ORGANISM: Artificial
<220> FEATURE:
<223> OTHER INFORMATION: barcode

<400> SEQUENCE: 1
atggacgcgt ggagt                                                      15

<210> SEQ ID NO 2
<211> LENGTH: 35
<212> TYPE: DNA
<213> ORGANISM: Artificial
<220> FEATURE:
<223> OTHER INFORMATION: Barcode sequence yaaA-bc

<400> SEQUENCE: 2
atggacgcgt ggagtgggtg ggtaaatggt aatgc                                35

<210> SEQ ID NO 3
<211> LENGTH: 35
<212> TYPE: DNA
<213> ORGANISM: Artificial
<220> FEATURE:

<223> OTHER INFORMATION: Barcode sequence yaaJ-bc

<400> SEQUENCE: 3
atggacgcgt ggagttccga cggggagtat atact                                35

<210> SEQ ID NO 4
<211> LENGTH: 35
<212> TYPE: DNA
<213> ORGANISM: Artificial
<220> FEATURE:
<223> OTHER INFORMATION: Barcode sequence talB-bc

<400> SEQUENCE: 4
atggacgcgt ggagtcatgt ttaggaacgc taccg                                35

<210> SEQ ID NO 5
<211> LENGTH: 35
<212> TYPE: DNA
<213> ORGANISM: Artificial
<220> FEATURE:
<223> OTHER INFORMATION: Barcode sequence mog-bc

<400> SEQUENCE: 5
atggacgcgt ggagtgtaca tgaaacgatg gacgg                                35

<210> SEQ ID NO 6
<211> LENGTH: 282
<212> TYPE: DNA
<213> ORGANISM: Escherichia coli

<400> SEQUENCE: 6
atgctgattc ttatttcacc tgcgaaaacg cttgattacc aaagcccgtt gaccaccacg     60
cgctatacgc tgccggagct gttagacaat tcccagcagt tgatccatga ggcgcggaaa    120
ctgacgcctc cgcagattag cacgctgatg cgcatcagcg acaaactggc gggtatcaac    180
gccgctcgct tcatgactg gcagccagat ttcacgccgg cgaatgcccg ccaggcgatt     240
ctggcgttta aggtgatgt ctacaccggc ttgcaggccg aa                        282

<210> SEQ ID NO 7
<211> LENGTH: 277
<212> TYPE: DNA
<213> ORGANISM: Escherichia coli

<400> SEQUENCE: 7
atgccagatt ttttctcctt cattaacagc gtcctttggg gatcggtaat gatttacctg     60
ctcttcggcg caggttgttg gttcactttt cgcaccggat tgtgcagtt tcgctacatc    120 cgccagtttg gcaaaagtct taaaaatagc attcatccac agccaggcgg tttaacctca    180
tttcagtcat tgtgtaccag tcttgcggcg cgcgtgggta gcggcaacct ggccggcgtt    240
gcgctggcta ttaccgccgg tggacctgga gccgtct                             277

<210> SEQ ID NO 8
<211> LENGTH: 290
<212> TYPE: DNA
<213> ORGANISM: Escherichia coli

<400> SEQUENCE: 8
atgacggaca aattgacctc ccttcgtcag tacaccaccg tagtggccga cactggggac     60
atcgcggcaa tgaagctgta tcaaccgcag gatgccacaa ccaacccttc tctcattctt    120
aacgcagcgc agattccgga ataccgtaag ttgattgatg atgctgtcgc ctgggcgaaa    180

```
cagcagagca acgatcgcgc gcagcagatc gtggacgcga ccgacaaact ggcagtaaat    240
attggtctgg aaatcctgaa actggttccg ggccgtatct caactgaagt               290
```

<210> SEQ ID NO 9
<211> LENGTH: 280
<212> TYPE: DNA
<213> ORGANISM: Escherichia coli

<400> SEQUENCE: 9

```
atgaatactt tacgtattgg cttagtttcc atctctgatc gcgcatccag cggcgtttat    60
caggataaag gcatccctgc gctggaagaa tggctgacat cggcgctaac cacgccgttt    120
gaactggaaa cccgcttaat ccccgatgag caggcgatca tcgagcaaac gttgtgtgag    180
ctggtggatg aaatgagttg ccatctggtg ctcaccacgg gcggaactgg cccggcgcgt    240
cgtgacgtaa cgcccgatgc gacgctggca gtagcggacc                         280
```

<210> SEQ ID NO 10
<211> LENGTH: 15
<212> TYPE: DNA
<213> ORGANISM: Artificial
<220> FEATURE:
<223> OTHER INFORMATION: primer

<400> SEQUENCE: 10

```
actcgacggc ctctg                                                     15
```

<210> SEQ ID NO 11
<211> LENGTH: 15
<212> TYPE: DNA
<213> ORGANISM: Artificial
<220> FEATURE:
<223> OTHER INFORMATION: primer

<400> SEQUENCE: 11

```
acacgcgcgt tgaag                                                     15
```

<210> SEQ ID NO 12
<211> LENGTH: 144
<212> TYPE: DNA
<213> ORGANISM: Artificial
<220> FEATURE:
<223> OTHER INFORMATION: primer

<400> SEQUENCE: 12

```
tcaactgctg ggaattgtct aacagctccg gcagcgtata gcgcgtggtg gtcaacgggc    60
tttggtaatc aagcgttttc gcaggtgaaa taagaatcag catcagaggc cgtcgagtca    120
ctgcgcatta ccatttaccc accc                                           144
```

<210> SEQ ID NO 13
<211> LENGTH: 144
<212> TYPE: DNA
<213> ORGANISM: Artificial
<220> FEATURE:
<223> OTHER INFORMATION: primer sequence yaaJ-L

<400> SEQUENCE: 13

```
caaatccggt gcgaaaagtg aaccaacaac ctgcgccgaa gagcaggtaa atcattaccg    60
atccccaaag gacgctgtta atgaaggaga aaaaatctgg catcagaggc cgtcgagtca    120
ctgcagtata tactcccccgt cgga                                          144
```

<210> SEQ ID NO 14
<211> LENGTH: 144
<212> TYPE: DNA
<213> ORGANISM: Artificial
<220> FEATURE:
<223> OTHER INFORMATION: primer sequence talB-L

<400> SEQUENCE: 14

```
tggttgtggc atcctgcggt tgatacagct tcattgccgc gatgtcccca gtgtcggcca    60
ctacggtggt gtactgacga agggaggtca atttgtccgt catcagaggc cgtcgagtca   120
ctgccggtag cgttcctaaa catg                                          144
```

<210> SEQ ID NO 15
<211> LENGTH: 144
<212> TYPE: DNA
<213> ORGANISM: Artificial
<220> FEATURE:
<223> OTHER INFORMATION: primer sequence mog-L

<400> SEQUENCE: 15

```
ccgatgtcag ccattcttcc agcgcaggga tgcctttatc ctgataaacg ccgctggatg    60
cgcgatcaga gatggaaact aagccaatac gtaaagtatt catcagaggc cgtcgagtca   120
ctgcccgtcc atcgtttcat gtac                                          144
```

<210> SEQ ID NO 16
<211> LENGTH: 144
<212> TYPE: DNA
<213> ORGANISM: Artificial
<220> FEATURE:
<223> OTHER INFORMATION: primer sequence yaaA-M

<400> SEQUENCE: 16

```
tcatgaaagc gagcggcgtt gatacccgcc agtttgtcgc tgatgcgcat cagcgtgcta    60
atctgcggag cgtcagtttt ccgcgcctca tggatcaact gctgggaatt gtctaacaca   120
ctgcgcatta ccatttaccc accc                                          144
```

<210> SEQ ID NO 17
<211> LENGTH: 144
<212> TYPE: DNA
<213> ORGANISM: Artificial
<220> FEATURE:
<223> OTHER INFORMATION: primer sequence yaaJ-M

<400> SEQUENCE: 17

```
tggtacacaa tgactgaaat gaggttaaac cgcctggctg tggatgaatg ctatttttaa    60
gacttttgcc aaactggcgg atgtagcgaa actgcacaaa tccggtgcga aaagtgaaca   120
ctgcagtata tactccccgt cgga                                          144
```

<210> SEQ ID NO 18
<211> LENGTH: 144
<212> TYPE: DNA
<213> ORGANISM: Artificial
<220> FEATURE:
<223> OTHER INFORMATION: primer sequence talB-M

<400> SEQUENCE: 18

```
tgcgcgcgat cgttgctctg ctgtttcgcc caggcgacag catcatcaat caacttacgg    60
tattccggaa tctgcgctgc gttaagaatg agagaagggt tggttgtggc atcctgcgca   120
ctgccggtag cgttcctaaa catg                                          144
```

<210> SEQ ID NO 19
<211> LENGTH: 144
<212> TYPE: DNA
<213> ORGANISM: Artificial
<220> FEATURE:
<223> OTHER INFORMATION: primer sequence mog-M

<400> SEQUENCE: 19
caactcattt catccaccag ctcacacaac gtttgctcga tgatcgcctg ctcatcgggg      60
attaagcggg tttccagttc aaacggcgtg gttagcgccg atgtcagcca ttcttccaca     120
ctgcccgtcc atcgtttcat gtac                                            144

<210> SEQ ID NO 20
<211> LENGTH: 144
<212> TYPE: DNA
<213> ORGANISM: Artificial
<220> FEATURE:
<223> OTHER INFORMATION: primer sequence yaaA-R

<400> SEQUENCE: 20
acacgcgcgt tgaagttcgg cctgcaagcc ggtgtagaca tcacctttaa acgccagaat      60
cgcctggcgg gcattcgccg gcgtgaaatc tggctgccag tcatgaaagc gagcggcgca    120
ctgcgcatta ccatttaccc accc                                            144

<210> SEQ ID NO 21
<211> LENGTH: 144
<212> TYPE: DNA
<213> ORGANISM: Artificial
<220> FEATURE:
<223> OTHER INFORMATION: primer sequence yaaJ-R

<400> SEQUENCE: 21
acacgcgcgt tgaagagacg gctccaggtc caccggcggt aatagccagc gcaacgccgg      60
ccaggttgcc gctacccacg cgcgccgcaa gactggtaca caatgactga aatgaggtca    120
ctgcagtata tactccccgt cgga                                            144

<210> SEQ ID NO 22
<211> LENGTH: 144
<212> TYPE: DNA
<213> ORGANISM: Artificial
<220> FEATURE:
<223> OTHER INFORMATION: primer sequence talB-R

<400> SEQUENCE: 22
acacgcgcgt tgaagacttc agttgagata cggcccggaa ccagtttcag gatttccaga      60
ccaatattta ctgccagttt gtcggtcgcg tccacgatct gctgcgcgcg atcgttgcca    120
ctgccggtag cgttcctaaa catg                                            144

<210> SEQ ID NO 23
<211> LENGTH: 144
<212> TYPE: DNA
<213> ORGANISM: Artificial
<220> FEATURE:
<223> OTHER INFORMATION: primer sequence mog-R

<400> SEQUENCE: 23
acacgcgcgt tgaagggtcc gctactgcca gcgtcgcatc gggcgttacg tcacgacgcg      60
ccgggccagt tccgcccgtg gtgagcacca gatggcaact catttcatcc accagctcca    120

```
ctgcccgtcc atcgtttcat gtac                                              144

<210> SEQ ID NO 24
<211> LENGTH: 15
<212> TYPE: DNA
<213> ORGANISM: Artificial
<220> FEATURE:
<223> OTHER INFORMATION: PCR primer bc-amp-F

<400> SEQUENCE: 24
atggacgcgt ggagt                                                         15

<210> SEQ ID NO 25
<211> LENGTH: 15
<212> TYPE: DNA
<213> ORGANISM: Artificial
<220> FEATURE:
<223> OTHER INFORMATION: PCR primer bc-amp-R

<400> SEQUENCE: 25
tagggctccg cttgg                                                         15

<210> SEQ ID NO 26
<211> LENGTH: 15
<212> TYPE: DNA
<213> ORGANISM: Artificial
<220> FEATURE:
<223> OTHER INFORMATION: PCR primer asmblyfwd

<400> SEQUENCE: 26
actcgacggc ctctg                                                         15

<210> SEQ ID NO 27
<211> LENGTH: 15
<212> TYPE: DNA
<213> ORGANISM: Artificial
<220> FEATURE:
<223> OTHER INFORMATION: PCR primer asmblyrev

<400> SEQUENCE: 27
acacgcgcgt tgaag                                                         15

<210> SEQ ID NO 28
<211> LENGTH: 15
<212> TYPE: DNA
<213> ORGANISM: Artificial
<220> FEATURE:
<223> OTHER INFORMATION: Primer chpampfwd

<400> SEQUENCE: 28
cgagccgtgg ttcct                                                         15

<210> SEQ ID NO 29
<211> LENGTH: 15
<212> TYPE: DNA
<213> ORGANISM: Artificial
<220> FEATURE:
<223> OTHER INFORMATION: Primer chpamprev

<400> SEQUENCE: 29
cgctgggagg gtgtt                                                         15

<210> SEQ ID NO 30
<211> LENGTH: 15
<212> TYPE: DNA
<213> ORGANISM: Artificial
```

```
<220> FEATURE:
<223> OTHER INFORMATION: Forward Primer bc-amp-F

<400> SEQUENCE: 30
atggacgcgt ggagt                                                15

<210> SEQ ID NO 31
<211> LENGTH: 15
<212> TYPE: DNA
<213> ORGANISM: Artificial
<220> FEATURE:
<223> OTHER INFORMATION: Reverse Primer bc-rev-BioT-R

<400> SEQUENCE: 31
tagggctccg cttgg                                                15

<210> SEQ ID NO 32
<211> LENGTH: 15
<212> TYPE: DNA
<213> ORGANISM: Artificial
<220> FEATURE:
<223> OTHER INFORMATION: assembly oligonucleotide

<400> SEQUENCE: 32
cgagccgtgg ttcct                                                15

<210> SEQ ID NO 33
<211> LENGTH: 14
<212> TYPE: DNA
<213> ORGANISM: Artificial
<220> FEATURE:
<223> OTHER INFORMATION: assembly oligonucleotide

<400> SEQUENCE: 33
cgctgggagg gtgt                                                 14

<210> SEQ ID NO 34
<211> LENGTH: 15
<212> TYPE: DNA
<213> ORGANISM: Artificial
<220> FEATURE:
<223> OTHER INFORMATION: Forward Primer

<400> SEQUENCE: 34
cgagccgtgg ttcct                                                15

<210> SEQ ID NO 35
<211> LENGTH: 14
<212> TYPE: DNA
<213> ORGANISM: Artificial
<220> FEATURE:
<223> OTHER INFORMATION: Reverse Primer

<400> SEQUENCE: 35
cgctgggagg gtgt                                                 14
```

ASSEMBLY OF NUCLEIC ACID SEQUENCES IN EMULSIONS

RELATED APPLICATION

This application is a National Stage Application under 35 U.S.C. 371 of PCT application PCT/US2013/026045 designating the United States and filed Feb. 14, 2013; which claims the benefit of U.S. Provisional Patent Application No. 61/600,118, filed on Feb. 17, 2012 each of which are hereby incorporated by reference in their entireties.

STATEMENT OF GOVERNMENT INTERESTS

This invention was made with government support under N000141010144 awarded by the Office of Naval Research, FG02-02ER63445 awarded by the Department of Energy, W911NF-08-1-0254 awarded by the Defense Advanced Research Projects Agency, and HG003170 awarded by the National Institutes of Health. The government has certain rights in the invention.

BACKGROUND

Field of the Invention

Embodiments of the present invention relate in general to methods and compositions for assembling nucleic acid sequences.

Description of Related Art

The development of inexpensive, high-throughput and reliable gene synthesis methods will broadly stimulate progress in biology and biotechnology (Carr & Church (2009) *Nat. Biotechnol.* 27:1151). Currently, the reliance on column-synthesized oligonucleotides as a source of DNA limits further cost reductions in gene synthesis (Tian et al. (2009) *Mol. BioSyst.* 5:714). Oligonucleotides from DNA microchips can reduce costs by at least an order of magnitude, yet efforts to scale microchip use have been largely unsuccessful due to the high error rates and complexity of the oligonucleotide mixtures (Tian et al. (2004) *Nature* 432:1050; Richmond et al. (2004) *Nucleic Acids Res.* 32:5011; Zhou et al. (2004) *Nucleic Acids Res.* 32:5409).

The synthesis of novel DNA encoding regulatory elements, genes, pathways, and entire genomes provides powerful ways to both test biological hypotheses as well as harness biology for humankind's use. For example, since the initial use of oligonucleotides in deciphering the genetic code, DNA synthesis has engendered tremendous progress in biology with the recent complete synthesis of a viable bacterial genome (Nirenberg et al. (1961) *Proc. Natl. Acad. Sci. USA* 47:1588; Söll et al. (1965) *Proc. Natl. Acad. Sci. USA* 54:1378; Gibson et al. (2010) *Science* 329:52). Currently, almost all DNA synthesis relies on the use of phosphoramidite chemistry on controlled-pore glass (CPG) substrates. CPG oligonucleotides synthesized in this manner are effectively limited to approximately 100 bases by the yield and accuracy of the process. Thus, the synthesis of gene-sized fragments relies on assembling many oligonucleotides together using a variety of techniques termed gene synthesis (Tian (2009) (supra); Gibson (supra); Gibson (2009) *Nucleic Acids Res.* 37:6984; Li & Elledge (2007) *Nat. Methods* 4:251; Bang & Church (2008) *Nat. Methods* 5:37; Shao et al. (2009) *Nucleic Acids Res.* 37:e16).

The price of gene synthesis has reduced drastically over the last decade as the process has become increasingly industrialized. However, the current commercial price of gene synthesis, approximately $0.40-1.00/bp, has begun to approach the relatively stable cost of the CPG oligonucleotide precursors (approximately $0.10-0.20/bp) (Carr (supra)). At these prices, the construction of large gene libraries and synthetic genomes is out of reach to most. To achieve further cost reductions, many current efforts focus on smaller volume synthesis of oligonucleotides in order to minimize reagent costs. For example, microfluidic oligonucleotide synthesis can reduce reagent cost by an order of magnitude (Lee et al. (2010) *Nucleic Acids Res.* 38:2514).

Another route is to harness existing DNA microchips, which can produce up to a million different oligonucleotides on a single chip, as a source of DNA for gene synthesis. Previous efforts have demonstrated the ability to synthesize genes from DNA microchips. Tian et al. described the assembly of 14.6 kb of novel DNA from 292 oligonucleotides synthesized on an Atactic/Xeotron chip (Tian (2004) (supra)). The process involved using 584 short oligonucleotides synthesized on the same chip for hybridization-based error correction. The resulting error rates were approximately 1/160 basepairs (bp) before error correction and approximately 1/1400 bp after. Using similar chips, Zhou et al. constructed approximately 12 genes with an error rate as low as 1/625 bp (Zhou (supra)). Richardson et al. showed the assembly of an 180 bp construct from eight oligonucleotides synthesized on a microarray using maskless photolithographic deprotection (Nimblegen) (Richmond (supra)). Though the error rates were not determined in that study, a follow-up construction of a 742 bp green fluorescent protein (GFP) sequence using the same process showed an error rate of 1/20 bp-1/70 bp (Kim et al. (2006) *Microelectronic Eng.* 83:1613). These approaches have thus far failed to scale for at least two reasons. First, the error rates of chip-based oligonucleotides from DNA microchips are higher than traditional column-synthesized oligonucleotides. Second, the assembly of gene fragments becomes increasingly difficult as the diversity of the oligonucleotide mixture becomes larger.

SUMMARY

The present invention provides methods and compositions to isolate or co-locate one or more oligonucleotide sequences (e.g., DNA and/or RNA sequences) from more complex mixtures of oligonucleotide sequences and create assembled nucleic acid sequences of interest (e.g., DNA and/or RNA sequences (e.g., genes, genomes and the like)). According to one aspect, oligonucleotides of a complex mixture are isolated or co-located within emulsion droplets. According to an additional aspect, assembled nucleic acids are created within the emulsion droplets. According to a still further aspect, methods are provided to create long synthetic nucleic acid pools or gene libraries using short nucleic acids such as oligonucleotides which may be produced of obtained from plates or arrays of synthetic oligonucleotides. According to this aspect amplification and/or assembly of nucleic acid sequences is carried out using bead based emulsions. The present invention further provides methods for generating oligonucleotide primers (e.g., orthogonal primers) that are useful for synthesizing one or more nucleic acid sequences of interest (e.g., gene(s), genome(s) and the like). The present invention further provides barcodes and a barcoded library, such as a barcoded bead library, for use in the methods described herein.

According to one aspect, a mixture of subsequence oligonucleotides is divided into a plurality of localized sets of subsequence oligonucleotides. According to one aspect, each set of subsequence oligonucleotides is sequestered or otherwise contained within an emulsion droplet and the set of subsequence oligonucleotides is assembled into one or more assembled oligonucleotides.

According to one aspect, a method is provided to sequester or co-locate oligonucleotides into emulsion droplets and then assemble the oligonucleotides into a target nucleic acid sequence. The oligonucleotides within the emulsion droplet may be members or a subportion of a larger mixture of oligonucleotides. The oligonucleotides within the emulsion droplet may be referred to herein as subsequences and the subsequences may be assembled into the target nucleic acid sequence. In this manner, the subsequence oligonucleotides are used to build the target nucleic acid sequence. Accordingly, the target nucleic acid sequence is generally longer than the individual subsequences.

According to one aspect, a method is provided to sequester or co-locate oligonucleotides into emulsion droplets and then assemble the oligonucleotides into a plurality of nucleic acid sequences, one of which may be a target nucleic acid sequence. The oligonucleotides within the emulsion droplet may be members or a subportion of a larger mixture of oligonucleotides. The oligonucleotides within the emulsion droplet may be referred to herein as subsequences and the subsequences may be assembled into the plurality of nucleic acid sequences. In this manner, the subsequence oligonucleotides are used to build the plurality of nucleic acid sequences. Accordingly, members of the plurality of nucleic acid sequences are generally longer than the individual subsequences.

According to one aspect, a method of isolating subportions of a mixture of oligonucleotides is provided including localizing a plurality of oligonucleotide subsequences defining an oligonucleotide set within the mixture of oligonucleotides by hybridization to a predesigned sequence or barcode that is unique to each oligonucleotide set. According to an additional aspect, the oligonucleotide set corresponds to a particular target nucleic acid sequence. According to an additional aspect, the plurality of oligonucleotide subsequences defining an oligonucleotide set is isolated within an emulsion droplet.

According to one aspect, a method of synthesizing a target nucleic acid sequence is provided including localizing a plurality of oligonucleotide subsequences defining an oligonucleotide set corresponding to a particular target nucleic acid sequence by hybridization to a predesigned sequence or barcode that is unique to each oligonucleotide set, attaching the plurality of oligonucleotide subsequences to a bead, placing the bead within an emulsion droplet, separating the plurality of oligonucleotide subsequences from the bead such that the plurality of oligonucleotide subsequences remain within the emulsion droplet, and assembling within the emulsion droplet the plurality of oligonucleotide subsequences to form the target nucleic acid sequence. The plurality of oligonucleotide subsequences within the emulsion droplet may be members or a subportion of a larger mixture of oligonucleotides.

According to one aspect, a method of synthesizing a plurality of target nucleic acid sequences is provided including localizing a plurality of oligonucleotide subsequences defining a plurality of oligonucleotide sets with each oligonucleotide set corresponding to a particular target nucleic acid sequence by hybridization to a predesigned sequence or barcode that is unique to each oligonucleotide set, for each oligonucleotide set, attaching a plurality of oligonucleotide subsequences corresponding to an oligonucleotide set to a bead, placing the bead within an emulsion droplet, separating the plurality of oligonucleotide subsequences from the bead such that the plurality of oligonucleotide subsequences remain within the emulsion droplet, and assembling within the emulsion droplet the plurality of oligonucleotide subsequences to form one of the target nucleic acid sequences. The plurality of oligonucleotide subsequences within the emulsion droplet may be members or a subportion of a larger mixture of oligonucleotides.

According to one aspect, a method of synthesizing a target nucleic acid sequence is provided including amplifying a plurality of oligonucleotide subsequences defining an oligonucleotide set corresponding to a particular target nucleic acid sequence by using orthogonal primers that hybridize to a pair of orthogonal primer binding sites that are unique to the oligonucleotide set, removing the orthogonal primer binding sites from the amplified plurality of oligonucleotide subsequences, attaching the amplified plurality of oligonucleotide subsequences to a bead, synthesizing a complementary strand to each of the amplified plurality of oligonucleotide subsequences to produce a plurality of double stranded nucleic acids, placing the bead within an emulsion droplet, separating the plurality of double stranded nucleic acids from the bead such that the plurality of double stranded nucleic acids remain within the emulsion droplet, and assembling within the emulsion droplet the plurality of double stranded nucleic acids to form the target nucleic acid sequence. The plurality of oligonucleotide subsequences within the emulsion droplet may be members or a subportion of a larger mixture of oligonucleotides.

A method of synthesizing a plurality of target nucleic acid sequences is provided including, for each target nucleic acid sequence within the plurality, localizing a plurality of oligonucleotide subsequences defining an oligonucleotide set corresponding to a particular target nucleic acid sequence by hybridization to a predesigned sequence that is unique to the oligonucleotide set thereby resulting in a plurality of oligonucleotide sets corresponding to the plurality of target nucleic acid sequences, attaching the plurality of oligonucleotide sets to a plurality of beads, placing the plurality of beads within a plurality of emulsion droplets, separating the plurality of double stranded nucleic acids from the bead such that the plurality of double stranded nucleic acids remain within the emulsion droplet; and assembling within the emulsion droplet the plurality of double stranded nucleic acids to form one of the plurality of target nucleic acid sequences.

According to one aspect, a method of synthesizing a plurality of target nucleic acid sequences is provided including amplifying a plurality of oligonucleotide subsequences defining a plurality of oligonucleotide sets with each oligonucleotide set corresponding to a particular target nucleic acid sequence by using orthogonal primers that hybridize to a pair of orthogonal primer binding site sequences that are unique to each oligonucleotide set, removing the orthogonal primer binding sites from the amplified plurality of oligonucleotide subsequences, for each oligonucleotide set, attaching corresponding amplified oligonucleotide subsequences defining the set to a bead, synthesizing a complementary strand to each of the amplified oligonucleotide subsequences to produce a plurality of double stranded nucleic acids, placing the bead within an emulsion droplet, separating the plurality of double stranded nucleic acids from the bead such that the plurality of double stranded nucleic acids remain within the emulsion droplet, and assembling within the emulsion droplet the plurality of double stranded nucleic acids to form one of the plurality of target nucleic acid sequences. The plurality of oligonucleotide subsequences within the emulsion droplet may be members or a subportion of a larger mixture of oligonucleotides.

According to one aspect, libraries useful in the present disclosure need not be amplified to create useful oligonucleotides. For example, oligonucleotides can be obtained from microarrays or chips or synthesized for use in the methods described herein.

In certain exemplary embodiments, microarrays including at least 5,000 different oligonucleotide sequences are provided. Each oligonucleotide sequence of the microarray is a member of one of a plurality of oligonucleotide sets, and each oligonucleotide set is specific for a nucleic acid sequence of interest (e.g., a single nucleic acid sequence of interest). Each oligonucleotide sequence that is a member of a particular oligonucleotide set includes a pair of orthogonal primer binding sites having a sequence that is unique to said oligonucleotide set. The nucleic acid sequence of interest is at least 20, 30, 40, 50, 60, 70, 80, 90, 100, 200, 300, 400, or 500 nucleotides in length. In certain aspects, at least 50, at least 100, or more oligonucleotide sets are provided wherein each set is specific for a unique nucleic acid sequence of interest. In other aspects, the oligonucleotide sequence of interest is at least 1,000, at least 2,500, at least 5,000, or more nucleotides in length. In still other aspects, the nucleic acid sequence of interest is a DNA sequence, e.g., a regulatory element, a gene, a pathway and/or a genome. In still other aspects, the microarray includes at least 10,000 different oligonucleotide sequences attached thereto.

In certain exemplary embodiments, a microarray comprising at least 10,000 different oligonucleotide sequences attached thereto is provided. Each oligonucleotide sequence of the microarray is a member of one of at least 50 oligonucleotide sets, and each oligonucleotide set is specific for a nucleic acid sequence of interest. Each oligonucleotide sequence that is a member of a particular oligonucleotide set includes a pair of orthogonal primer binding sites having a sequence that is unique to said oligonucleotide set. Each nucleic acid sequence of interest is at least 2,500 nucleotides in length.

In certain exemplary embodiments, methods of synthesizing a nucleic acid sequence of interest are provided. The methods include the steps of providing at least 5,000 different oligonucleotide sequences, wherein each oligonucleotide sequence is a member of one of a plurality of oligonucleotide sets, and each oligonucleotide set is specific for a nucleic acid sequence of interest. Each oligonucleotide sequence includes a pair of orthogonal primer binding sites having a sequence that is unique to a single oligonucleotide set. The methods include the step of amplifying an oligonucleotide set using orthogonal primers that hybridize to the orthogonal primer binding sites unique to the set, and removing the orthogonal primer binding sites from the amplified oligonucleotide set. The methods further include the step of assembling the amplified oligonucleotide set into a nucleic acid sequence of interest that is at least 20, 30, 40, 50, 60, 70, 80, 90, 100, 200, 300, 400 or 500 nucleotides in length. In certain aspects, the nucleic acid sequence of interest is at least 1,000, at least 2,500, at least 5,000, or more nucleotides in length. In other aspects, the nucleic acid sequence of interest is a DNA sequence, e.g., a regulatory element, a gene, a pathway and/or a genome. In yet other aspects, 50, 100, 500, 750, 1,000 or more oligonucleotide sets are provided, wherein each set is specific for a unique nucleic acid sequence of interest. In still other aspects, the 5,000 different oligonucleotide sequences are provided on a microarray and, optionally, the 5,000 different oligonucleotide sequences can be removed from the microarray prior to the step of amplifying.

According to certain aspects of the present disclosure, synthetic nucleic acid sequences are created from complex pools of nucleic acids produced from plates or arrays of synthetic oligonucleotides. According to one aspect, a target nucleic acid sequence is assembled from a plurality of subsequences. The subsequences have a length shorter that the target nucleic acid sequence. Amplification and assembly of nucleic acid sequences may be carried out using bead based emulsion techniques described herein.

Further features and advantages of certain embodiments of the present invention will become more fully apparent in the following description of the embodiments and drawings thereof, and from the claims.

DETAILED DESCRIPTION

The present invention provides methods and compositions for the localization of one or more sets of subsequence oligonucleotides from among a plurality of subsequence oligonucleotides, such as a mixture of subsequence oligonucleotides. According to one aspect, each set of the one or more sets of subsequence oligonucleotides is used to assemble one or more assembled nucleic acid sequences. Accordingly, one aspect is directed to assembly of one or more nucleic acid sequences of interest from a large pool of oligonucleotide sequences.

According to one aspect, a set of subsequence oligonucleotides is sequestered or localized or contained within an emulsion droplet. According to an additional aspect, a plurality of emulsion droplets is provided with each including a set of subsequence oligonucleotides. According to a still additional aspect, the emulsion droplet includes the set of subsequence oligonucleotides and reagents sufficient to assemble the subsequence oligonucleotides into one or more assembled nucleic acid sequences.

According to one aspect, subsequence oligonucleotides collectively forming an oligonucleotide set are localized by hybridization to a predesigned sequence or barcode that is unique to each oligonucleotide set. The oligonucleotide set can correspond to a particular target nucleic acid sequence. The localized oligonucleotide set can be assembled into an assembled nucleic acid sequence, such as an assembled target nucleic acid sequence. According to one aspect, the localized oligonucleotide set can be attached to a bead. The bead can then be sequestered or contained within an emulsion droplet. The oligonucleotide set can then be detached from the bead and contained within the emulsion droplet. The detached oligonucleotide set within the emulsion droplet can then be assembled into one or more assembled nucleic acid sequences in the presence of suitable reagents within the emulsion droplet and with the emulsion droplet under suitable reaction conditions.

Figure 1:
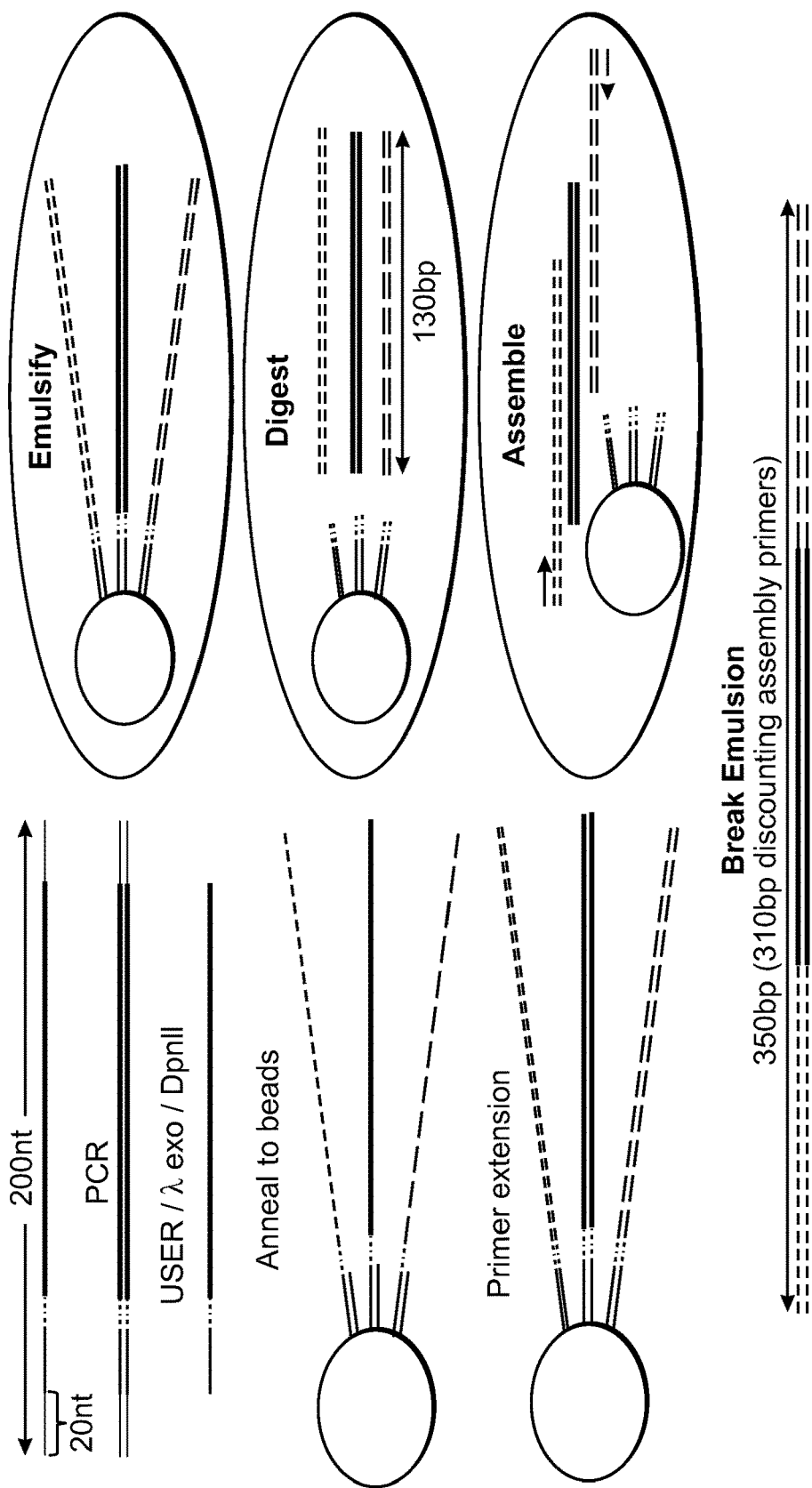
FIG. 1 is a schematic depicting an emulsion assembly process of the present disclosure.

FIG. 1 depicts an exemplary embodiment of a method for the multiplexed assembly of oligonucleotides in emulsion. As depicted in FIG. 1, DNA from microarrays are amplified, and then processed to remove primers and make single stranded DNA (ssDNA). Each individual assembly has a specific barcode that localizes all the oligonucleotides necessary to create a nucleic acid sequence onto a bead. The beads are then emulsified with a single bead being contained within an emulsion droplet. A TypeIIs restriction enzyme digests the oligonucleotide at a point to remove the oligonucleotides from the bead leaving the barcode attached to the bead. The freed or detached oligonucleotides within the emulsion droplet are then assembled within the emulsion droplet by PCR using common primers and reagents. The emulsion droplets are broken and the assembled constructs are collected thereby resulting in large libraries of assembled constructs from DNA microchips.

According to one aspect, a barcoded bead library is provided including a plurality of beads with each bead having a set of oligonucleotides attached thereto. Each oligonucleotide within the set includes the same barcode. The barcode can be predesigned or it can be a randomly generated sequence.

In certain exemplary embodiments, an assembled nucleic acid sequence which may also be referred to herein as a nucleic acid sequence of interest or a target nucleic acid sequence is at least about 20, 30, 40, 50, 60, 70, 80, 90, 100, 200, 300, 400, 500 600, 700, 800, 900, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 1,000,000, 2,000,000, 3,000,000, 4,000,000, 5,000,000, 6,000,000, 7,000,000, 8,000,000, 9,000,000, 10,000,000 or more nucleotides in length. In other exemplary embodiments, a nucleic acid sequence of interest is between 100 and 10,000,000 nucleic acids in length, including any ranges therein. In yet other exemplary embodiments, a nucleic acid sequence of interest is between 100 and 20,000 nucleic acids in length, including any ranges therein. In still other exemplary embodiments, a nucleic acid sequence of interest is between 100 and 25,000 nucleic acids in length, including any ranges therein. In still other exemplary embodiments, a nucleic acid sequence of interest is between 300 and 5,000 nucleic acids in length, including any ranges therein. In other aspects, a nucleic acid sequence of interest is a DNA sequence such as, e.g., a regulatory element (e.g., a promoter region, an enhancer region, a coding region, a non-coding region and the like), a gene, a genome, a pathway (e.g., a metabolic pathway (e.g., nucleotide metabolism, carbohydrate metabolism, amino acid metabolism, lipid metabolism, co-factor metabolism, vitamin metabolism, energy metabolism and the like), a signaling pathway, a biosynthetic pathway, an immunological pathway, a developmental pathway and the like) and the like. In yet other aspects, a nucleic acid sequence of interest is the length of a gene, e.g., between about 500 nucleotides and 5,000 nucleotides in length. In still other aspects, a nucleic acid sequence of interest is the length of a genome (e.g., a phage genome, a viral genome, a bacterial genome, a fungal genome, a plant genome, an animal genome or the like).

In certain exemplary aspects, oligonucleotide sequences are provided which include a barcode sequence. The barcode is used to identify or encode a group or collection of oligonucleotide sequences. The barcode sequence may be randomly generated or it may be a predesigned sequence. According to one aspect, a plurality of oligonucleotide sequences may have the same barcode sequence, and accordingly, form an oligonucleotide set. The set of oligonucleotides which may be within a larger collection of oligonucleotides may be localized or co-located by using the barcode.

Embodiments of the present invention are directed to oligonucleotide sequences having two or more orthogonal primer binding sites that each hybridizes to an orthogonal primer. As used herein, the term "orthogonal primer binding site" is intended to include, but is not limited to, a nucleic acid sequence located at the 5' and/or 3' end of the oligonucleotide sequences of the present invention which hybridizes a complementary orthogonal primer. An "orthogonal primer pair" refers to a set of two primers of identical sequence that bind to both orthogonal primer binding sites at the 5' and 3' ends of each oligonucleotide sequence of an oligonucleotide set. Orthogonal primer pairs are designed to be mutually non-hybridizing to other orthogonal primer pairs, to have a low potential to cross-hybridize with one another or with oligonucleotide sequences, to have a low potential to form secondary structures, and to have similar melting temperatures (Tms) to one another. Orthogonal primer pair design and software useful for designing orthogonal primer pairs is discussed further herein.

According to one aspect, an "oligonucleotide set" refers to a collection of oligonucleotides that can be used to assemble or otherwise create an assembled nucleic acid sequence. Such an oligonucleotide set can refer to a collection of oligonucleotides that correspond to a particular target nucleic acid to be assembled. In certain aspects, a nucleic acid sequence of interest is synthesized from a plurality of oligonucleotide sequences that make up an oligonucleotide set.

As used herein, the term "oligonucleotide set" may also refer to a set of oligonucleotide sequences that has identical orthogonal pair primer sites or identical barcodes and is specific for a nucleic acid sequence of interest. In certain aspects, a nucleic acid sequence of interest is synthesized from a plurality of oligonucleotide sequences that make up an oligonucleotide set. In other aspects, the plurality of oligonucleotide sequences that make up an oligonucleotide set are retrieved from a large pool of heterogeneous oligonucleotide sequences via common barcodes or orthogonal primer binding sites. In certain aspects, an article of manufacture (e.g., a microchip, a test tube, a kit or the like) is provided that includes a plurality of oligonucleotide sequences encoding a mixture of oligonucleotide sets.

In certain exemplary embodiments, at least 100, 200, 300, 400, 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 30,000, 35,000, 40,000, 45,000, 50,000, 55,000, 60,000, 65,000, 70,000, 75,000, 80,000, 85,000, 90,000, 95,000, 100,000 or more different oligonucleotide sequences are provided. In certain aspects, between about 2,000 and about 80,000 different oligonucleotide sequences are provided. In other aspects, between about 5,000 and about 60,000 different oligonucleotide sequences are provided. In still other aspects, about 55,000 different oligonucleotide sequences are provided.

In certain exemplary embodiments, the oligonucleotide sequences are at least 20, 30, 40, 50, 60, 70, 80, 90, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, 1000 or more nucleotides in length. In certain aspects, the oligonucleotide sequences are between about 50 and about 500 nucleotides in length. In other aspects, the oligonucleotide sequences are between about 100 and about 300 nucleotides in length. In other aspects, the oligonucleotide sequences are about 130 nucleotides in length. In still other aspects, the oligonucleotide sequences are about 200 nucleotides in length.

In certain exemplary embodiments, the oligonucleotide sequences encode at least 5, 10, 15, 20, 25, 30, 35, 40, 45, 50, 55, 60, 65, 70, 75, 80, 85, 90, 95, 100, 200, 300, 400, 500, 600, 700, 800, 900, 1,000, 2,000, 3,000, 4,000, 5,000, 6,000, 7,000, 8,000, 9,000, 10,000 or more different oligonucleotide sets.

In certain exemplary embodiments, at least 5, 10, 15, 20, 25, 30, 35, 40, 45, 50, 55, 60, 65, 70, 75, 80, 85, 90, 95, 100, 200, 300, 400, 500, 600, 700, 800, 900, 1,000, 2,000, 3,000, 4,000, 5,000, 6,000, 7,000, 8,000, 9,000, 10,000 different orthogonal primer pairs are provided.

In certain exemplary embodiments, methods are provided for synthesizing between about 1 to about 100,000 target nucleic acid sequences, between about 1 to about 75,000 target nucleic acid sequences, between about 1 to about 50,000 target nucleic acid sequences, between about 1 to about 10,000 target nucleic acid sequences, between about 100 to about 5,000 target nucleic acid sequences, between about 500 to about 1,000 target nucleic acid sequences or any range or value in between whether overlapping or not. According to certain aspects, methods are provided for simultaneously synthesizing between about 1 to about 10,000 target nucleic acid sequences, between about 100 to about 5,000 target nucleic acid sequences, between about 500 to about 1,000 target nucleic acid sequences or any range or value in between whether overlapping or not. The synthesis of a plurality of target nucleic acids describe herein is considered simultaneous to the extent that a plurality of emulsion droplets are created with each droplet within the plurality of droplets having an oligonucleotide set therein under conditions and with reagents capable of synthesizing a target nucleic acid sequence. Accordingly, each emulsion droplet is considered a discrete reaction volume within which a target nucleic acid sequence is synthesized. Accordingly, methods of the present disclosure include synthesizing between about 1 and about 10,000 target nucleic acids having lengths between about 300 to about 5,000 nucleotides. Still accordingly, methods of the present disclosure include synthesizing within emulsion droplets between about 1 and about 10,000 target nucleic acids having lengths between about 300 to about 5,000 nucleotides. According to a certain aspect, one target nucleic acid is synthesized within a single emulsion droplet. According to a certain aspect, a plurality of target nucleic acids are synthesized simultaneously within an emulsion where a target nucleic acid is synthesized in each of a plurality of emulsion droplets.

In certain exemplary embodiments, assembly PCR is used to produce a nucleic acid sequence of interest from a plurality of oligonucleotide sequences that are members of a particular oligonucleotide set. "Assembly PCR" refers to the synthesis of long, double stranded nucleic acid sequences by performing PCR on a pool of oligonucleotides having overlapping segments. Assembly PCR is discussed further in Stemmer et al. (1995) *Gene* 164:49. In certain aspects, PCR assembly is used to assemble single stranded nucleic acid sequences (e.g., ssDNA) into a nucleic acid sequence of interest. In other aspects, PCR assembly is used to assemble double stranded nucleic acid sequences (e.g., dsDNA) into a nucleic acid sequence of interest.

In certain exemplary embodiments, methods are provided for designing a set of end-overlapping oligonucleotides for each nucleic acid sequence of interest (e.g., a gene, a regulatory element, a pathway, a genome or the like) that alternates on both the plus and minus strands and are useful for assembly PCR. In another aspect, oligonucleotide design is aided by a computer program, e.g. a computer program using algorithms as described herein.

In certain exemplary embodiments, various error correction methods are provided to remove errors in oligonucleotide sequences, subassemblies and/or nucleic acid sequences of interest. The term "error correction" refers to a process by which a sequence error in a nucleic acid molecule is corrected (e.g., an incorrect nucleotide at a particular location is changed to the nucleic acid that should be present based on the predetermined sequence). Methods for error correction include, for example, homologous recombination or sequence correction using DNA repair proteins.

The term "DNA repair enzyme" refers to one or more enzymes that correct errors in nucleic acid structure and sequence, i.e., recognizes, binds and corrects abnormal base-pairing in a nucleic acid duplex. Examples of DNA repair enzymes include, but are not limited to, proteins such as mutH, mutL, mutM, mutS, mutY, dam, thymidine DNA glycosylase (TDG), uracil DNA glycosylase, AlkA, MLH1, MSH2, MSH3, MSH6, Exonuclease I, T4 endonuclease V, Exonuclease V, RecJ exonuclease, FEN1 (RAD27), dnaQ (mutD), polC (dnaE), or combinations thereof, as well as homologs, orthologs, paralogs, variants, or fragments of the forgoing. In certain exemplary embodiments, the ErrASE system is used for error correction (Novici Biotech, Vacaville, Calif.). Enzymatic systems capable of recognition and correction of base pairing errors within the DNA helix have been demonstrated in bacteria, fungi and mammalian cells and the like.

Terms and symbols of nucleic acid chemistry, biochemistry, genetics, and molecular biology used herein follow those of standard treatises and texts in the field, e.g., Kornberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See Kanehisa (1984) *Nucl. Acids Res.* 12:203.

"Complex" refers to an assemblage or aggregate of molecules in direct or indirect contact with one another. In one aspect, "contact," or more particularly, "direct contact," in reference to a complex of molecules or in reference to specificity or specific binding, means two or more molecules are close enough so that attractive noncovalent interactions, such as van der Waal forces, hydrogen bonding, ionic and hydrophobic interactions, and the like, dominate the interaction of the molecules. In such an aspect, a complex of molecules is stable in that under assay conditions the complex is thermodynamically more favorable than a non-aggregated, or non-complexed, state of its component molecules. As used herein, "complex" refers to a duplex or triplex of polynucleotides or a stable aggregate of two or more proteins. In regard to the latter, a complex is formed by an antibody specifically binding to its corresponding antigen.

"Duplex" refers to at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g., conditions including temperature of about 5° C. less that the $T_m$ of a strand of the duplex and low monovalent salt concentration, e.g., less than 0.2 M, or less than 0.1 M. "Perfectly matched" in reference to a duplex means that the polynucleotide or oligonucleotide strands making up the duplex form a double stranded structure with one another such that every nucleotide in each strand undergoes Watson-Crick base pairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" refers to a contiguous subregion or segment of a genome. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length. Usually, a particular genetic locus may be identified by its nucleotide sequence, or the nucleotide sequence, or sequences, of one or both adjacent or flanking regions. In another aspect, a genetic locus refers to the expressed nucleic acid product of a gene, such as an RNA molecule or a cDNA copy thereof.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual,* 2nd Ed. Cold Spring Harbor Press (1989) and Anderson *Nucleic Acid Hybridization,* $1^{st}$ Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Kit" refers to any delivery system for delivering materials or reagents for carrying out a method of the invention. In the context of assays, such delivery systems include systems that allow for the storage, transport, or delivery of reaction reagents (e.g., primers, enzymes, microarrays, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials for assays of the invention. Such contents may be delivered to the intended recipient together or separately. For example, a first container may contain an enzyme for use in an assay, while a second container contains primers.

"Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool (1999) *Nucl. Acids Res.* 27:875; Higgins et al., *Meth. in Enzymol.* (1979) 68:50; Engler et al. (1982) *The Enzymes,* 15:3 (1982); and Namsaraev, U.S. Patent Pub. 2004/0110213.

"Amplifying" includes the production of copies of a nucleic acid molecule of the array or a nucleic acid molecule bound to a bead via repeated rounds of primed enzymatic synthesis. "In situ" amplification indicates that the amplification takes place with the template nucleic acid molecule positioned on a support or a bead, rather than in solution. In situ amplification methods are described in U.S. Pat. No. 6,432,360.

"Support" can refer to a matrix upon which nucleic acid molecules of a nucleic acid array are placed. The support can be solid or semi-solid or a gel. "Semi-solid" refers to a compressible matrix with both a solid and a liquid component, wherein the liquid occupies pores, spaces or other interstices between the solid matrix elements. Semi-solid supports can be selected from polyacrylamide, cellulose, polyamide (nylon) and crossed linked agarose, dextran and polyethylene glycol.

"Randomly-patterned" or "random" refers to non-ordered, non-Cartesian distribution (in other words, not arranged at pre-determined points along the x- or y-axes of a grid or at defined "clock positions," degrees or radii from the center of a radial pattern) of nucleic acid molecules over a support, that is not achieved through an intentional design (or program by which such design may be achieved) or by placement of individual nucleic acid features. Such a "randomly-patterned" or "random" array of nucleic acids may be achieved by dropping, spraying, plating or spreading a solution, emulsion, aerosol, vapor or dry preparation comprising a pool of nucleic acid molecules onto a support and allowing the nucleic acid molecules to settle onto the support without intervention in any manner to direct them to specific sites thereon. Arrays of the invention can be randomly patterned or random.

"Heterogeneous" refers to a population or collection of nucleic acid molecules that comprises a plurality of different sequences. According to one aspect, a heterogeneous pool of oligonucleotide sequences is provided with an article of manufacture (e.g., a microarray).

"Nucleoside" as used herein includes the natural nucleosides, including 2'-deoxy and 2'-hydroxyl forms, e.g. as described in Komberg and Baker, *DNA Replication*, 2nd Ed. (Freeman, San Francisco, 1992). "Analogs" in reference to nucleosides includes synthetic nucleosides having modified base moieties and/or modified sugar moieties, e.g., described by Scheit, *Nucleotide Analogs* (John Wiley, New York, 1980); Uhlman and Peyman, *Chemical Reviews,* 90:543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al., *Exp. Opin. Ther. Patents,* 6: 855-870 (1996); Mesmaeker et al., *Current Opinion in Structural Biology,* 5:343-355 (1995); and the like. Exemplary types of polynucleotides that are capable of enhancing duplex stability include oligonucleotide phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Oligonucleotide" or "polynucleotide," which are used synonymously, means a linear polymer of natural or modified nucleosidic monomers linked by phosphodiester bonds or analogs thereof. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleosides, ribonucleosides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

Usually nucleosidic monomers are linked by phosphodiester bonds. Whenever an oligonucleotide is represented by a sequence of letters, such as "ATGCCTG," it will be understood that the nucleotides are in 5' to 3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs. It is clear to those skilled in the art when oligonucleotides having natural or non-natural nucleotides may be employed in methods and processes described herein. For example, where processing by an enzyme is called for, usually oligonucleotides consisting solely of natural nucleotides are required. Likewise, where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al., *Molecular Cloning,* Second Edition (Cold Spring Harbor Laboratory, New York, 1989), and like references. Oligonucleotides and polynucleotides may be single stranded or double stranded.

"Polymorphism" or "genetic variant" means a substitution, inversion, insertion, or deletion of one or more nucleotides at a genetic locus, or a translocation of DNA from one genetic locus to another genetic locus. In one aspect, polymorphism means one of multiple alternative nucleotide sequences that may be present at a genetic locus of an individual and that may comprise a nucleotide substitution, insertion, or deletion with respect to other sequences at the same locus in the same individual, or other individuals within a population. An individual may be homozygous or heterozygous at a genetic locus; that is, an individual may have the same nucleotide sequence in both alleles, or have a different nucleotide sequence in each allele, respectively. In one aspect, insertions or deletions at a genetic locus comprises the addition or the absence of from 1 to 10 nucleotides at such locus, in comparison with the same locus in another individual of a population (or another allele in the same individual). Usually, insertions or deletions are with respect to a major allele at a locus within a population, e.g., an allele present in a population at a frequency of fifty percent or greater.

"Primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of between 3 to 36 nucleotides, also 5 to 24 nucleotides, also from 14 to 36 nucleotides. Primers within the scope of the invention include orthogonal primers, amplification primers, constructions primers and the like. Pairs of primers can flank a sequence of interest or a set of sequences of interest. Primers and probes can be degenerate in sequence. Primers within the scope of the present invention bind adjacent to a target sequence (e.g., an oligonucleotide sequence of an oligonucleotide set or a nucleic acid sequence of interest).

In certain exemplary embodiments, barcodes or orthogonal primers/primer binding sites are designed to be temporary, e.g., to permit removal of the barcodes or orthogonal primers/primer binding sites at a desired stage prior to and/or during assembly. Temporary barcodes or orthogonal primers/primer binding sites may be designed so as to be removable by chemical, thermal, light-based, or enzymatic cleavage. Cleavage may occur upon addition of an external factor (e.g., an enzyme, chemical, heat, light, etc.) or may occur automatically after a certain time period (e.g., after n rounds of amplification). In one embodiment, temporary barcodes or orthogonal primers/primer binding sites may be removed by chemical cleavage. For example, barcodes or orthogonal primers/primer binding sites having acid labile or base labile sites may be used for amplification. The amplified pool may then be exposed to acid or base to remove the barcodes or orthogonal primer/primer binding sites at the desired location. Alternatively, the temporary barcodes or primers may be removed by exposure to heat and/or light. For example, barcodes or orthogonal primers/primer binding sites having heat labile or photolabile sites may be used for amplification. The amplified pool may then be exposed to heat and/or light to remove the barcodes or orthogonal primer/primer binding sites at the desired location. In another embodiment, an RNA primer may be used for amplification thereby forming short stretches of RNA/DNA hybrids at the ends of the nucleic acid molecule. The barcodes or orthogonal primers/primer binding sites may then be removed by exposure to an RNase (e.g., RNase H). In various embodiments, the method for removing the barcode or primer may only cleave a single strand of the amplified duplex thereby leaving 3' or 5' overhangs. Such overhangs may be removed using an exonuclease to form blunt ended double stranded duplexes. For example, $RecJ_f$ may be used to remove single stranded 5' overhangs and Exonuclease I or Exonuclease T may be used to remove single stranded 3' overhangs. Additionally, $S_1$ nuclease, $P_1$ nuclease, mung bean nuclease, and CEL I nuclease, may be used to remove single stranded regions from a nucleic acid molecule. $RecJ_f$, Exonuclease I, Exonuclease T, and mung bean nuclease are commercially available, for example, from New England Biolabs (Beverly, Mass.). S1 nuclease, P1 nuclease and CEL I nuclease are described, for example, in Vogt, V. M., *Eur. J. Biochem.*, 33: 192-200 (1973); Fujimoto et al., *Agric. Biol. Chem.* 38: 777-783 (1974); Vogt, V. M., *Methods Enzymol.* 65: 248-255 (1980); and Yang et al., *Biochemistry* 39: 3533-3541 (2000).

In one embodiment, the barcodes or temporary orthogonal primers/primer binding sites may be removed from a nucleic acid by chemical, thermal, or light based cleavage. Exemplary chemically cleavable internucleotide linkages for use in the methods described herein include, for example, β-cyano ether, 5'-deoxy-5'-aminocarbamate, 3' deoxy-3'-aminocarbamate, urea, 2' cyano-3', 5'-phosphodiester, 3'-(S)-phosphorothioate, 5'-(S)-phosphorothioate, 3'-(N)-phosphoramidate, 5'-(N)-phosphoramidate, α-amino amide, vicinal diol, ribonucleoside insertion, 2'-amino-3',5'-phosphodiester, allylic sulfoxide, ester, silyl ether, dithioacetal, 5'-thio-furmal, α-hydroxy-methyl-phosphonic bisamide, acetal, 3'-thio-furmal, methylphosphonate and phosphotriester. Internucleoside silyl groups such as trialkylsilyl ether and dialkoxysilane are cleaved by treatment with fluoride ion. Base-cleavable sites include β-cyano ether, 5'-deoxy-5'-aminocarbamate, 3'-deoxy-3'-aminocarbamate, urea, 2'-cyano-3',5'-phosphodiester, 2'-amino-3', 5'-phosphodiester, ester, and ribose. Thio-containing internucleotide bonds such as 3'-(S)-phosphorothioate and 5'-(S)-phosphorothioate are cleaved by treatment with silver nitrate or mercuric chloride. Acid cleavable sites include 3'-(N)-phosphoramidate, 5'-(N)-phosphoramidate, dithioacetal, acetal and phosphonic bisamide. An α-aminoamide internucleoside bond is cleavable by treatment with isothiocyanate, and titanium may be used to cleave a 2'-amino-3',5'-phosphodiester-O-ortho-benzyl internucleoside bond. Vicinal diol linkages are cleavable by treatment with periodate. Thermally cleavable groups include allylic sulfoxide and cyclohexene while photo-labile linkages include nitrobenzylether and thymidine dimer. Methods synthesizing and cleaving nucleic acids containing chemically cleavable, thermally cleavable, and photo-labile groups are described for example, in U.S. Pat. No. 5,700,642.

In other embodiments, temporary barcodes or orthogonal primers/primer binding sites may be removed using enzymatic cleavage. For example, barcodes or orthogonal primers/primer binding sites may be designed to include a restriction endonuclease cleavage site. After amplification, the pool of nucleic acids may be contacted with one or more endonucleases to produce double stranded breaks thereby removing the barcodes or primers/primer binding sites. In certain embodiments, the forward and reverse primers may be removed by the same or different restriction endonucleases. Any type of restriction endonuclease may be used to remove the barcodes or primers/primer binding sites from nucleic acid sequences. A wide variety of restriction endonucleases having specific binding and/or cleavage sites are commercially available, for example, from New England Biolabs (Ipswich, Mass.). In various embodiments, restriction endonucleases that produce 3' overhangs, 5' overhangs or blunt ends may be used. When using a restriction endonuclease that produces an overhang, an exonuclease (e.g., $RecJ_f$, Exonuclease I, Exonuclease T, $S_1$ nuclease, $P_1$ nuclease, mung bean nuclease, CEL I nuclease, etc.) may be used to produce blunt ends. In an exemplary embodiment, an orthogonal primer/primer binding site that contains a binding and/or cleavage site for a type IIS restriction endonuclease may be used to remove the barcode or temporary orthogonal primer binding site As used herein, the term "restriction endonuclease recognition site" is intended to include, but is not limited to, a particular nucleic acid sequence to which one or more restriction enzymes bind, resulting in cleavage of a DNA molecule either at the restriction endonuclease recognition sequence itself, or at a sequence distal to the restriction endonuclease recognition sequence. Restriction enzymes include, but are not limited to, type I enzymes, type II enzymes, type IIS enzymes, type III enzymes and type IV enzymes. The REBASE database provides a comprehensive database of information about restriction enzymes, DNA methyltransferases and related proteins involved in restriction-modification. It contains both published and unpublished work with information about restriction endonuclease recognition sites and restriction endonuclease cleavage sites, isoschizomers, commercial availability, crystal and sequence data (see Roberts et al. (2005) *Nucl. Acids Res.* 33:D230, incorporated herein by reference in its entirety for all purposes).

In certain aspects, barcodes or primers of the present invention include one or more restriction endonuclease recognition sites that enable type IIS enzymes to cleave the nucleic acid several base pairs 3' to the restriction endonuclease recognition sequence. As used herein, the term "type IIS" refers to a restriction enzyme that cuts at a site remote from its recognition sequence. Type IIS enzymes are known to cut at a distance from their recognition sites ranging from 0 to 20 base pairs. Examples of Type IIs endonucleases include, for example, enzymes that produce a 3' overhang, such as, for example, Bsr I, Bsm I, BstF5 I, BsrD I, Bts I, Mnl I, BciV I, Hph I, Mbo II, Eci I, Acu I, Bpm I, Mme I, BsaX I, Bcg I, Bae I, Bfi I, TspDT I, TspGW I, Taq II, Eco57 I, Eco57M I, Gsu I, Ppi I, and Psr I; enzymes that produce a 5' overhang such as, for example, BsmA I, Ple I, Fau I, Sap I, BspM I, SfaN I, Hga I, Bvb I, Fok I, BceA I, BsmF I, Ksp632 I, Eco31 I, Esp3 I, Aar I; and enzymes that produce a blunt end, such as, for example, Mly I and Btr I. Type-IIs endonucleases are commercially available and are well known in the art (New England Biolabs, Beverly, Mass.). Information about the recognition sites, cut sites and conditions for digestion using type IIs endonucleases may be found, for example, on the Worldwide web at neb.com/nebecomm/enzymefindersearch bytypeIIs.asp). Restriction endonuclease sequences and restriction enzymes are well known in the art and restriction enzymes are commercially available (New England Biolabs, Ipswich, Mass.).

Barcodes or primers (e.g., orthogonal primers, amplification primers, construction primers and the like) suitable for use in the methods disclosed herein may be designed with the aid of a computer program, such as, for example, DNAWorks, Gene2Oligo, or using the parameters software described herein. Typically, barcodes or primers are from about 5 to about 500, about 10 to about 100, about 10 to about 50, or about 10 to about 30 nucleotides in length. In certain exemplary embodiments, a set of barcodes or orthogonal primers or a plurality of sets of barcodes or orthogonal primers are designed so as to have substantially similar melting temperatures to facilitate manipulation of a complex reaction mixture. The melting temperature may be influenced, for example, by barcode or primer length and nucleotide composition. In certain exemplary embodiments, a plurality of sets of orthogonal primers are designed such that each set of orthogonal primers is mutually non-hybridizing with one another. Methods for designing orthogonal primers are described further herein.

"Solid support," "support," and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide. Semisolid supports and gel supports are also useful in the present invention.

"Specific" or "specificity" in reference to the binding of one molecule to another molecule, such as a target sequence to a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecule in a reaction or sample, it forms the largest number of the complexes with the second molecule. In certain aspects, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as van der Waal forces, hydrogen bonding, base-stacking interactions, ionic and hydrophobic interactions, and the like, dominate the interaction of the molecules.

"Spectrally resolvable" in reference to a plurality of fluorescent labels means that the fluorescent emission bands of the labels are sufficiently distinct, i.e., sufficiently non-overlapping, that molecular tags to which the respective labels are attached can be distinguished on the basis of the fluorescent signal generated by the respective labels by standard photodetection systems, e.g., employing a system of band pass filters and photomultiplier tubes, or the like, as exemplified by the systems described in U.S. Pat. Nos. 4,230,558; 4,811,218, or the like, or in Wheeless et al., pgs. 21-76, in *Flow Cytometry: Instrumentation and Data Analysis* (Academic Press, New York, 1985). In one aspect, spectrally resolvable organic dyes, such as fluorescein, rhodamine, and the like, means that wavelength emission maxima are spaced at least 20 nm apart, and in another aspect, at least 40 nm apart. In another aspect, chelated lanthanide compounds, quantum dots, and the like, spectrally resolvable means that wavelength emission maxima are spaced at least 10 nm apart, and in a further aspect, at least 15 nm apart.

"$T_m$" is used in reference to "melting temperature." Melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation. $T_m=81.5+0.41$ (% G+C), when a nucleic acid is in aqueous solution at 1 M NaCl (see e.g., Anderson and Young, "Quantitative Filter Hybridization," in *Nucleic Acid Hybridization* (1985). Other references (e.g., Allawi, H. T. & Santa Lucia, J., Jr., *Biochemistry* 36, 10581-94 (1997)) include alternative methods of computation which take structural and environmental, as well as sequence characteristics into account for the calculation of $T_m$.

In certain exemplary embodiments, oligonucleotide sequences are provided on a solid support. Oligonucleotide sequences may be synthesized on a solid support in an array format, e.g., a microarray of single stranded DNA segments synthesized in situ on a common substrate wherein each oligonucleotide is synthesized on a separate feature or location on the substrate. Arrays may be constructed, custom ordered, or purchased from a commercial vendor. Various methods for constructing arrays are well known in the art. For example, methods and techniques applicable to synthesis of construction and/or selection oligonucleotide synthesis on a solid support, e.g., in an array format have been described, for example, in WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752 and Zhou et al., Nucleic Acids Res. 32: 5409-5417 (2004).

Figure 5:
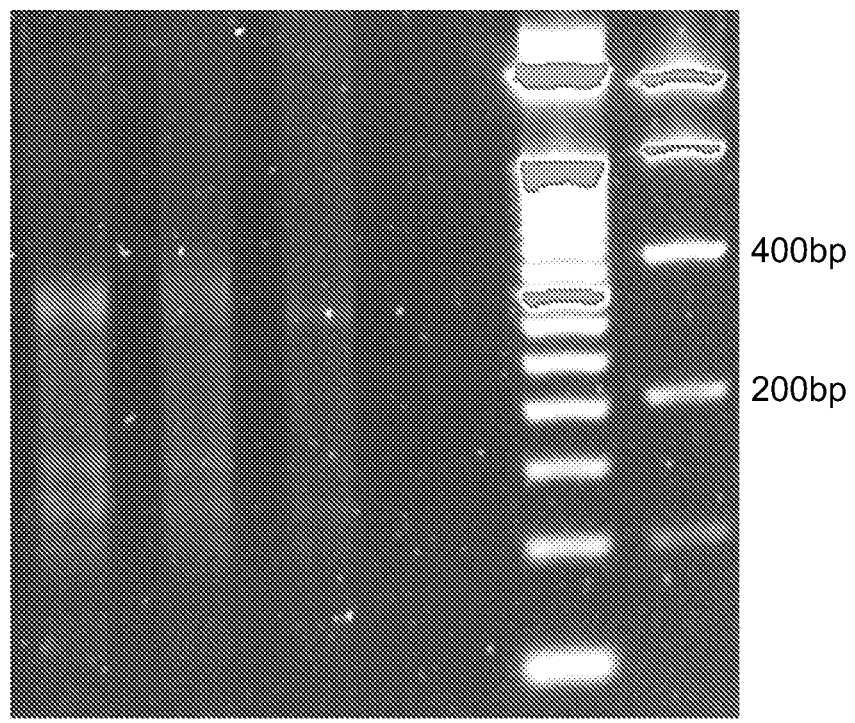
FIG. 5 is an imaged gel separation.

In an exemplary embodiment, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single stranded DNA molecule of desired sequence (See FIG. 5 of U.S. Pat. No. 6,375,903, based on the use of reflective optics). It is often desirable that a maskless array synthesizer is under software control. Since the entire process of microarray synthesis can be accomplished in only a few hours, and since suitable software permits the desired DNA sequences to be altered at will, this class of device makes it possible to fabricate microarrays including DNA segments of different sequences every day or even multiple times per day on one instrument. The differences in DNA sequence of the DNA segments in the microarray can also be slight or dramatic. The MAS instrument may be used in the form it would normally be used to make microarrays for hybridization experiments, but it may also be adapted to have features specifically adapted for the compositions, methods, and systems described herein. For example, it may be desirable to substitute a coherent light source, i.e. a laser, for the light source shown in FIG. 5 of the above-mentioned U.S. Pat. No. 6,375,903. If a laser is used as the light source, a beam expanded and scatter plate may be used after the laser to transform the narrow light beam from the laser into a broader light source to illuminate the micromirror arrays used in the maskless array synthesizer. It is also envisioned that changes may be made to the flow cell in which the microarray is synthesized. In particular, it is envisioned that the flow cell can be compartmentalized, with linear rows of array elements being in fluid communication with each other by a common fluid channel, but each channel being separated from adjacent channels associated with neighboring rows of array elements. During microarray synthesis, the channels all receive the same fluids at the same time. After the DNA segments are separated from the substrate, the channels serve to permit the DNA segments from the row of array elements to congregate with each other and begin to self-assemble by hybridization.

Other methods synthesizing construction and/or selection oligonucleotides include, for example, light-directed methods utilizing masks, flow channel methods, spotting methods, pin-based methods, and methods utilizing multiple supports.

Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be used as necessary. Other applicable methods include mechanical techniques such as those described in U.S. Pat. No. 5,384,261.

Additional methods applicable to synthesis of construction and/or selection oligonucleotides on a single support are described, for example, in U.S. Pat. No. 5,384,261. For example reagents may be delivered to the support by either (1) flowing within a channel defined on predefined regions or (2) "spotting" on predefined regions. Other approaches, as well as combinations of spotting and flowing, may be employed as well. In each instance, certain activated regions of the support are mechanically separated from other regions when the monomer solutions are delivered to the various reaction sites.

Flow channel methods involve, for example, microfluidic systems to control synthesis of oligonucleotides on a solid support. For example, diverse polymer sequences may be synthesized at selected regions of a solid support by forming flow channels on a surface of the support through which appropriate reagents flow or in which appropriate reagents are placed. One of skill in the art will recognize that there are alternative methods of forming channels or otherwise protecting a portion of the surface of the support. For example, a protective coating such as a hydrophilic or hydrophobic coating (depending upon the nature of the solvent) is utilized over portions of the support to be protected, sometimes in combination with materials that facilitate wetting by the reactant solution in other regions. In this manner, the flowing solutions are further prevented from passing outside of their designated flow paths.

Spotting methods for preparation of oligonucleotides on a solid support involve delivering reactants in relatively small quantities by directly depositing them in selected regions. In some steps, the entire support surface can be sprayed or otherwise coated with a solution, if it is more efficient to do so. Precisely measured aliquots of monomer solutions may be deposited dropwise by a dispenser that moves from region to region. Typical dispensers include a micropipette to deliver the monomer solution to the support and a robotic system to control the position of the micropipette with respect to the support, or an ink jet printer. In other embodiments, the dispenser includes a series of tubes, a manifold, an array of pipettes, or the like so that various reagents can be delivered to the reaction regions simultaneously.

Pin-based methods for synthesis of oligonucleotide sequences on a solid support are described, for example, in U.S. Pat. No. 5,288,514. Pin-based methods utilize a support having a plurality of pins or other extensions. The pins are each inserted simultaneously into individual reagent containers in a tray. An array of 96 pins is commonly utilized with a 96-container tray, such as a 96-well microtitre dish. Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously.

In yet another embodiment, a plurality of oligonucleotide sequences may be synthesized on multiple supports. One example is a bead based synthesis method which is described, for example, in U.S. Pat. Nos. 5,770,358, 5,639,603, and 5,541,061. For the synthesis of molecules such as oligonucleotides on beads, a large plurality of beads are suspended in a suitable carrier (such as water) in a container. The beads are provided with optional spacer molecules having an active site to which is complexed, optionally, a protecting group. At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. An individual bead may be tagged with a sequence which is unique to the double-stranded oligonucleotide thereon, to allow for identification during use.

Various exemplary protecting groups useful for synthesis of oligonucleotide sequences on a solid support are described in, for example, Atherton et al., 1989, Solid Phase Peptide Synthesis, IRL Press.

In various embodiments, the methods described herein utilize solid supports for immobilization of oligonucleotide sequences. For example, oligonucleotide sequences may be synthesized on one or more solid supports. Exemplary solid supports include, for example, slides, beads, chips, particles, strands, gels, sheets, tubing, spheres, containers, capillaries, pads, slices, films, or plates. In various embodiments, the solid supports may be biological, non-biological, organic, inorganic, or combinations thereof. When using supports that are substantially planar, the support may be physically separated into regions, for example, with trenches, grooves, wells, or chemical barriers (e.g., hydrophobic coatings, etc.). Supports that are transparent to light are useful when the assay involves optical detection (see e.g., U.S. Pat. No. 5,545,531). The surface of the solid support will typically contain reactive groups, such as carboxyl, amino, and hydroxyl or may be coated with functionalized silicon compounds (see e.g., U.S. Pat. No. 5,919,523).

In certain exemplary embodiments, the oligonucleotide sequences synthesized on the solid support may be used as a template for the production of oligonucleotides for assembly into longer polynucleotide constructs (e.g., nucleic acid sequences of interest). For example, the support-bound oligonucleotides may be contacted with primers that hybridize to the oligonucleotides under conditions that permit chain extension of the primers. The support bound duplexes may then be denatured and subjected to further rounds of amplification.

In other exemplary embodiments, the support bound oligonucleotide sequences may be removed from the solid support prior to amplification and/or assembly into polynucleotide constructs (e.g., nucleic acid sequences of interest). The oligonucleotides may be removed from the solid support, for example, by exposure to conditions such as acid, base, oxidation, reduction, heat, light, metal ion catalysis, displacement or elimination chemistry, or by enzymatic cleavage.

In certain embodiments, oligonucleotide sequences may be attached to a solid support through a cleavable linkage moiety. For example, the solid support may be functionalized to provide cleavable linkers for covalent attachment to the oligonucleotides. The linker moiety may be of six or more atoms in length. Alternatively, the cleavable moiety may be within an oligonucleotide and may be introduced during in situ synthesis. A broad variety of cleavable moieties are available in the art of solid phase and microarray oligonucleotide synthesis (see e.g., Pon, R., Methods Mol. Biol. 20:465-496 (1993); Verma et al., *Ann. Rev. Biochem.* 67:99-134 (1998); U.S. Pat. Nos. 5,739,386, 5,700,642 and 5,830,655; and U.S. Patent Publication Nos. 2003/0186226 and 2004/0106728). A suitable cleavable moiety may be selected to be compatible with the nature of the protecting group of the nucleoside bases, the choice of solid support, and/or the mode of reagent delivery, among others. In an exemplary embodiment, the oligonucleotides cleaved from the solid support contain a free 3'-OH end. Alternatively, the free 3'-OH end may also be obtained by chemical or enzymatic treatment, following the cleavage of oligonucleotides. The cleavable moiety may be removed under conditions which do not degrade the oligonucleotides. Preferably the linker may be cleaved using two approaches, either (a) simultaneously under the same conditions as the deprotection step or (b) subsequently utilizing a different condition or reagent for linker cleavage after the completion of the deprotection step.

The covalent immobilization site may either be at the 5' end of the oligonucleotide or at the 3' end of the oligonucleotide. In some instances, the immobilization site may be within the oligonucleotide (i.e. at a site other than the 5' or 3' end of the oligonucleotide). The cleavable site may be located along the oligonucleotide backbone, for example, a modified 3'-5' internucleotide linkage in place of one of the phosphodiester groups, such as ribose, dialkoxysilane, phosphorothioate, and phosphoramidate internucleotide linkage. The cleavable oligonucleotide analogs may also include a substituent on, or replacement of, one of the bases or sugars, such as 7-deazaguanosine, 5-methylcytosine, inosine, uridine, and the like.

In one embodiment, cleavable sites contained within the modified oligonucleotide may include chemically cleavable groups, such as dialkoxysilane, 3'-(S)-phosphorothioate, 5'-(S)-phosphorothioate, 3'-(N)-phosphoramidate, 5'-(N)phosphoramidate, and ribose. Synthesis and cleavage conditions of chemically cleavable oligonucleotides are described in U.S. Pat. Nos. 5,700,642 and 5,830,655. For example, depending upon the choice of cleavable site to be introduced, either a functionalized nucleoside or a modified nucleoside dimer may be first prepared, and then selectively introduced into a growing oligonucleotide fragment during the course of oligonucleotide synthesis. Selective cleavage of the dialkoxysilane may be effected by treatment with fluoride ion. Phosphorothioate internucleotide linkage may be selectively cleaved under mild oxidative conditions. Selective cleavage of the phosphoramidate bond may be carried out under mild acid conditions, such as 80% acetic acid. Selective cleavage of ribose may be carried out by treatment with dilute ammonium hydroxide.

In another embodiment, a non-cleavable hydroxyl linker may be converted into a cleavable linker by coupling a special phosphoramidite to the hydroxyl group prior to the phosphoramidite or H-phosphonate oligonucleotide synthesis as described in U.S. Patent Application Publication No. 2003/0186226. The cleavage of the chemical phosphorylation agent at the completion of the oligonucleotide synthesis yields an oligonucleotide bearing a phosphate group at the 3' end. The 3'-phosphate end may be converted to a 3' hydroxyl end by a treatment with a chemical or an enzyme, such as alkaline phosphatase, which is routinely carried out by those skilled in the art.

In another embodiment, the cleavable linking moiety may be a TOPS (two oligonucleotides per synthesis) linker (see e.g., PCT publication WO 93/20092). For example, the TOPS phosphoramidite may be used to convert a non-cleavable hydroxyl group on the solid support to a cleavable linker. A preferred embodiment of TOPS reagents is the Universal TOPS™ phosphoramidite. Conditions for Universal TOPS™ phosphoramidite preparation, coupling and cleavage are detailed, for example, in Hardy et al. *Nucleic Acids Research* 22(15):2998-3004 (1994). The Universal TOPS™ phosphoramidite yields a cyclic 3' phosphate that may be removed under basic conditions, such as the extended ammonia and/or ammonia/methylamine treatment, resulting in the natural 3' hydroxy oligonucleotide.

In another embodiment, a cleavable linking moiety may be an amino linker. The resulting oligonucleotides bound to the linker via a phosphoramidite linkage may be cleaved with 80% acetic acid yielding a 3'-phosphorylated oligonucleotide.

In another embodiment, the cleavable linking moiety may be a photocleavable linker, such as an ortho-nitrobenzyl photocleavable linker. Synthesis and cleavage conditions of photolabile oligonucleotides on solid supports are described, for example, in Venkatesan et al., *J. Org. Chem.* 61:525-529 (1996), Kahl et al., *J. Org. Chem.* 64:507-510 (1999), Kahl et al., *J. Org. Chem.* 63:4870-4871 (1998), Greenberg et al., *J. Org. Chem.* 59:746-753 (1994), Holmes et al., *J. Org. Chem.* 62:2370-2380 (1997), and U.S. Pat. No. 5,739,386. Ortho-nitobenzyl-based linkers, such as hydroxymethyl, hydroxyethyl, and Fmoc-aminoethyl carboxylic acid linkers, may also be obtained commercially.

In another embodiment, oligonucleotides may be removed from a solid support by an enzyme such as a nuclease. For example, oligonucleotides may be removed from a solid support upon exposure to one or more restriction endonucleases, including, for example, class IIs restriction enzymes. A restriction endonuclease recognition sequence may be incorporated into the immobilized oligonucleotides and the oligonucleotides may be contacted with one or more restriction endonucleases to remove the oligonucleotides from the support. In various embodiments, when using enzymatic cleavage to remove the oligonucleotides from the support, it may be desirable to contact the single stranded immobilized oligonucleotides with primers, polymerase and dNTPs to form immobilized duplexes. The duplexes may then be contacted with the enzyme (e.g., a restriction endonuclease) to remove the duplexes from the surface of the support. Methods for synthesizing a second strand on a support bound oligonucleotide and methods for enzymatic removal of support bound duplexes are described, for example, in U.S. Pat. No. 6,326,489. Alternatively, short oligonucleotides that are complementary to the restriction endonuclease recognition and/or cleavage site (e.g., but are not complementary to the entire support bound oligonucleotide) may be added to the support bound oligonucleotides under hybridization conditions to facilitate cleavage by a restriction endonuclease (see e.g., PCT Publication No. WO 04/024886).

According to certain aspects, a barcoded library is generated, such as a bead-based library having barcoded oligonucleotides attached thereto using methods known to those of ordinary skill. For example, individual biotinylated oligonucleotides can be synthesized, attached to beads having streptavidin attached thereto (strepavidin beads), and subsequently mixed to form a library of barcoded beads. Barcode sequences can be arbitrary sequences, or they can be designed to be orthogonal to one another. Attachment chemistries to the beads can vary using chemistries known to those of skill in the art such as biotin, carboxylation, and the like). Barcoded bead libraries as described herein can be repeatedly used for assembly methods described herein.

Figures 7, 8:
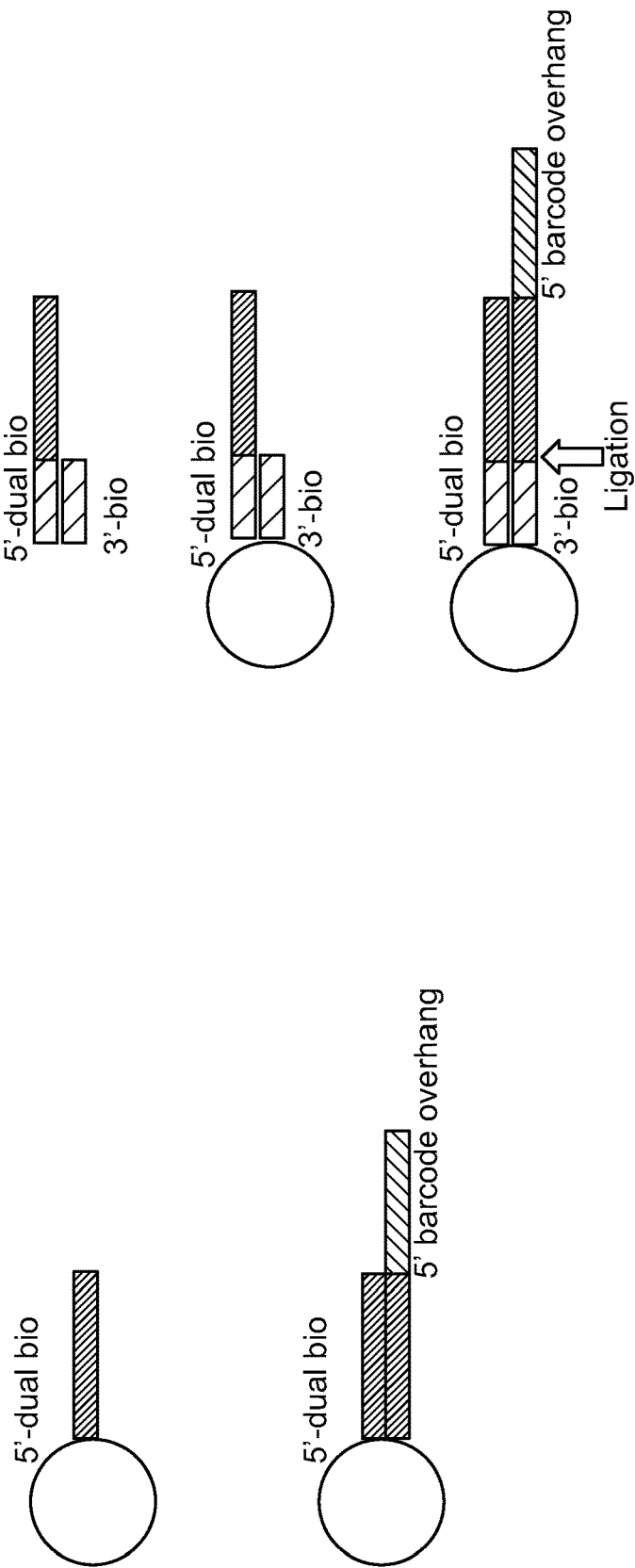
FIG. 7 is an illustration of one aspect of a bead with a nucleic acid barcode attached to the bead.
FIG. 8 is an illustration of one aspect of a bead with a nucleic acid barcode attached to the bead.

According to an additional aspect and with respect to FIG. 7, a barcoded bead is provided for use in the methods described herein. According to one aspect, a bead is provided to which is attached an anchor oligonucleotide, such as a single stranded anchor oligonucleotide, as shown in FIG. 7. The anchor oligonucleotide can be attached to a bead using methods known to those of skill in the art, such as an avidin-biotin binding pair or other known binding pairs or conjugates. For example, a 5' dual biotinylated anchor oligonucleotide (commercially available from Integrated DNA Technologies) is attached to a M270 Strepavidin bead (commercially available from Life Technologies.) The beads are then barcoded with a secondary oligonucleotide, such as a single stranded oligonucleotide, hybridizable with the anchor oligonucleotide as shown in FIG. 7. The secondary oligonucleotide hybridizes with or anneals to the anchor oligonucleotide. The secondary oligonucleotide includes a nucleic acid barcode sequence, such as a 5' nucleic acid barcode sequence, which is hybridizable with a complementary nucleic acid barcode sequence present on an oligonucleotide, such as an assembly oligonucleotide. The barcode sequence may be referred to as a "barcode overhang" or "5' barcode overhang" as it is the portion of the secondary oligonucleotide which does not hybridize with the anchor oligonucleotide. According to this aspect, the barcode sequence on the bead hybridizes or anneals with the complementary barcode sequence on an oligonucleotide so as to bind the oligonucleotide to the bead. According to one aspect, the bead includes a plurality of anchors to which are hybridized corresponding secondary oligonucleotides including barcode sequences. According to one aspect, the barcode sequences are the same as or are common to the bead. Accordingly, a bead is provided having a plurality of barcode sequences having a common nucleic acid sequence. The barcode sequences are able to bind a plurality of oligonucleotides sharing the complement to the common nucleic acid barcode sequence. In this exemplary manner, only oligonucleotides having the same complementary barcode sequence can bind to same barcode sequences on the bead. If a particular set of assembly oligonucleotides are provided with the same barcode sequence, the set of assembly oligonucleotides will bind to the same bead. Therefore, the set of assembly oligonucleotides can be located within an emulsion droplet for the making of a target nucleic acid.

According to an additional aspect shown in FIG. 8, a secondary nucleic acid is hybridized to an anchor oligonucleotide and ligated to the anchor oligonucleotide. According to one aspect, a partially double stranded nucleic acid is provided having a single stranded anchor oligonucleotide portion. The double stranded portion binds to the bead using methods known to those of skill in the art and described herein. That is the 5' end of a first strand and the 3' end of a second or complementary strand are bound to the bead using method known to those of skill in the art. For example, the 5' end of the first strand and the 3' end of the complementary strand may be biotinylated and then attached to an avidin or streptavidin moiety on a bead. The beads are then barcoded with a secondary oligonucleotide, such as a single stranded oligonucleotide, hybridizable with the anchor oligonucleotide portion as shown in FIG. 8. The secondary oligonucleotide hybridizes with or anneals to the anchor oligonucleotide. The adjacent nucleotides of the secondary oligonucleotide and the double stranded portion are ligated. Stated differently, the secondary oligonucleotide is ligated to the double stranded portion at the 3' strand. The secondary oligonucleotide includes a nucleic acid barcode sequence which is hybridizable with a complementary nucleic acid barcode sequence present on an oligonucleotide, such as an assembly oligonucleotide. The barcode sequence may be referred to as a "barcode overhang" as it is the portion of the secondary oligonucleotide which does not hybridize with the anchor oligonucleotide. According to this aspect, the barcode sequence on the bead hybridizes or anneals with the complementary barcode sequence on an oligonucleotide so as to bind the oligonucleotide to the bead. According to one aspect, the bead includes a plurality of partially double stranded nucleic acids each having a single stranded anchor oligonucleotide portion to which is hybridized a corresponding secondary oligonucleotide including a barcode sequence.

According to one aspect, the barcode sequences are the same as or are common to the bead. Accordingly, a bead is provided having a plurality of barcode sequences having a common nucleic acid sequence. The barcode sequences are able to bind a plurality of oligonucleotides sharing the complement to the common nucleic acid barcode sequence. In this exemplary manner, only oligonucleotides having the same complementary barcode sequence can bind to same barcode sequences on the bead. If a particular set of assembly oligonucleotides are provided with the same barcode sequence, the set of assembly oligonucleotides will bind to the same bead. Therefore, the set of assembly oligonucleotides can be located within an emulsion droplet for the making of a target nucleic acid.

According to an alternate aspect, a first bead-contacting oligonucleotide sequence is appended to an anchor oligonucleotide sequence. A second bead-contacting oligonucleotide sequence is hybridized to the first bead contacting oligonucleotide sequence to form a duplex or double stranded nucleic acid structure with the anchor oligonucleotide remaining as a single stranded nucleic acid. The duplex is then bound to the bead using methods known to those of skill in the art. For example, the ends of the first bead-contacting oligonucleotide sequence and the second bead-contacting oligonucleotide sequence in the duplex are biotinylated and are attached to M270 streptavidin beads. A secondary oligonucleotide including a barcode sequence is hybridized to the anchor oligonucleotide and ligated to the adjacent nucleotide of the duplex. The barcode sequence is available to hybridize to a complementary barcode sequence.

Barcoded bead libraries can be constructed from chips by emulsion PCR. Emulsion methods are known to those of skill in the art. Methods and reagents useful in the present disclosure are described in Shendure et al., *Science* 309 (5741):1728-32, Williams et al., *Nature Methods* 3:545-550 (2006), Diehl et al., *Nature Methods* 3:551-559 (2006) and Schutze et al., *Analytical Biochemistry* 410:155-157 (2011) each of which are hereby incorporated by reference in their entireties. Designed barcodes can be synthesized on chips with common PCR primers and a type IIs restriction enzyme recognition site on the 3' end internal to the PCR primer. The library is clonally amplified on beads using standard limited dilution emulsion PCR techniques such that only one barcode is amplified onto beads leaving a plurality of beads with no amplification product. The beads are then de-emulsified, and processed by the Type IIS restriction enzyme to remove the common PCR primer located distal to the attachment point. The DNA on the beads is then made single stranded by standard techniques such as NaOH elution. The beads may be further enriched using standard bead enrichment techniques used for high-throughput sequencing. These orthogonal bead libraries can be used for many assembly reactions depending on the scale of synthesis of the oligonucleotides or emulsion PCR.

The oligonucleotides according to the present disclosure which are used to assemble or create an assembled nucleic acid sequence can be synthesized using standard column-synthesized techniques or on DNA microchips. Oligonucleotides may be designed to have an barcode at the 3' end of their sequence, and type IIs restriction enzyme sites to remove the barcode and any amplification primers that may be present using methods known to those of skill in the art and described herein. For any individual assembly of a target nucleic acid, the oligonucleotides within the set of oligonucleotides, i.e. subsequence oligonucleotides, will contain the same barcode sequence, orthogonal or otherwise. The oligonucleotides may then be annealed to the orthogonal bead library, and a multiplex primer extension may then be carried out to produce a double stranded nucleic acid, such as double stranded DNA. According to this aspect, each bead includes oligonucleotides which are used to create a target nucleic acid sequence. In one aspect, the bead includes a set of oligonucleotide subsequences required to generate a target nucleic acid sequence.

In a certain aspect, a library of beads is emulsified in a buffer and enzyme mixture that contains a TypeIIs restriction enzyme, DNA polymerase, common primers, as well as additional reagents known to those of skill in the art and as described herein, to facilitate assembly. Bead emulsion techniques useful in the present methods are known to those of skill in the art. Methods and reagents useful in the present disclosure are described in Shendure et al., *Science* 309 (5741):1728-32, Williams et al., *Nature Methods* 3:545-550 (2006), Diehl et al., *Nature Methods* 3:551-559 (2006) and Schutze et al., *Analytical Biochemistry* 410:155-157 (2011) each of which are hereby incorporated by reference in their entireties. The emulsified mixture contains a plurality of beads which may be from at least 100 beads, at least 1000 beads, at least 10,000 beads, at least 100,000 beads, at least 1,000,000 beads and higher. According to one aspect, a plurality of beads are sequestered or contained within an emulsion droplet. According to one aspect, about 1 to about 5 beads are sequestered or contained within an emulsion droplet. According to one aspect, about 1 to about 2 beads are sequestered or contained within an emulsion droplet. According to one aspect, 1 bead or a single bead is sequestered or contained within an emulsion droplet.

The beads may be subject to temperature and reagents which remove the oligonucleotide sequences from the beads. For example, the beads may be incubated at a temperature which allows for a restriction enzyme to separate the oligonucleotides from the beads and in certain instances leaving the barcodes and primer sequences attached to the beads, and while not activating polymerase activity. The oligonucleotides are then contained within the emulsion droplet but are no longer attached to the beads. According to one aspect, the oligonucleotides are contained within the emulsion droplet along with reagents suitable for assembling the oligonucleotides into nucleic acids or a target nucleic acid. Polymerase activity may be activated by temperature sensitive reagents such that the polymerase is inactive at the temperature at which the restriction enzyme is active to detach the oligonucleotide from the bead. Similarly, the restriction enzyme may be deactivated at the temperature at which the polymerase is activated to assemble the oligonucleotides into a nucleic acid sequence.

Accordingly, various restriction enzymes may have different activities or efficiencies and so may be selected to be used with PCR reagents, such as PCR hotstart buffer, depending upon the temperature at which digestion by the restriction enzyme is to take place and the temperature at which oligonucleotide assembly is to take place. Representative enzymes and buffers are shown in Table 1 below.

| # | Enzyme | Template | Buffer |
|---|--------|----------|--------|
| 1 | BtsI | BtsI | Phusion |
| 2 | EarI | SapI | Phusion |
| 3 | MlyI | MlyI | Phusion |
| 4 | PleI | MlyI | Phusion |
| 5 | BmrI | BmrI | Phusion |
| 6 | AlwI | AlwI | Phusion |
| 7 | BccI | BccI | Phusion |
| 8 | BsaI | BsaI-HF | Phusion |
| 9 | BsaI-HF | BsaI-HF | Phusion |
| 10 | HpyAV | HpyAV | Phusion |
| 11 | SapI | SapI | Phusion |
| 12 | BbsI | BbsI | Phusion |
| 13 | BciVI | BciVI | Phusion |
| 14 | HphI | HphI | Phusion |
| 15 | MboII | BbsI | Phusion |
| 16 | BtsI | BtsI | KOD |
| 17 | EarI | SapI | KOD |
| 18 | MlyI | MlyI | KOD |
| 19 | PleI | MlyI | KOD |
| 20 | BmrI | BmrI | KOD |
| 21 | AlwI | AlwI | KOD |
| 22 | BccI | BccI | KOD |
| 23 | BsaI | BsaI-HF | KOD |
| 24 | BsaI-HF | BsaI-HF | KOD |
| 25 | HpyAV | HpyAV | KOD |
| 26 | SapI | SapI | KOD |
| 27 | BbsI | BbsI | KOD |
| 28 | BciVI | BciVI | KOD |
| 29 | HphI | HphI | KOD |
| 30 | MboII | BbsI | KOD |

According to certain aspects, the emulsion, and therefore the beads within the emulsion droplets, is thermal-cycled to assemble the oligonucleotides, such as double stranded DNA in each emulsion into nucleic acids, such as target nucleic acids, such as full length fragments. The mixture is then de-emulsified, and nucleic acids can be separated such as by gel purification or other methods known to those of skill in the art. De-emulsification protocols are known to those of skill in the art. See, for example, Schutze et al., *Analytical Biochemistry* 410:155-157 (2011). According to one aspect, nucleic acids can be separated and correctly assembled products of desired length can be isolated and recovered using standard gel electrophoresis techniques known to those of skill in the art. Accordingly, a library of specifically assembled sequences is constructed, which can be further isolated by PCR if necessary, or used directly as a library in other cases.

Oligonucleotides can be synthesized using methods known to those of skill in the art and described herein such as column-synthesis or chip synthesis or taken directly from a prefabricated chip and pooled. The oligonucleotides can be amplified before being processed into a library using methods known to those of skill in the art and described herein. According to one aspect, the oligonucleotides can be single stranded or double stranded. Double stranded oligonucleotides can be rendered single stranded using methods known to those of skill in the art and described herein. The oligonucleotides can include a barcode or primer. The barcode or primer can be included in the original synthesis of the oligonucleotide or it can be added to a fully formed oligonucleotide.

Barcodes and primers can be detached from the oligonucleotide using methods known to those of skill in the art and described herein. For example, a restriction enzyme recognition site can be present within the oligonucleotide and a restriction enzyme, such as a type IIs restriction enzyme or other restriction enzyme, can be used to cleave the oligonucleotide at or near the restriction enzyme recognition site thereby separating a barcode or primer from the remaining oligonucleotide sequence. Other methods and materials known to those of skill in the art can also be used to separate a barcode or primer from the remaining oligonucleotide sequence such as a USER enzyme.

A set of oligonucleotides can be used to create a target nucleic acid using methods known to those of skill in the art and described herein. The process of making a nucleic acid from the set of oligonucleotides may be referred to herein as "assembly." Assembly can occur using PCR, as described, or other techniques such as ligation. One exemplary method is isothermal assembly such as that described in Gibson et al., *Nature Methods* 6:343-345 (2009) hereby incorporated by reference in its entirety.

According to one aspect, nucleic acids made according to the methods described herein can be error corrected by the formation of hetero-duplexes in the emulsion using techniques known to those of skill in the art and described herein such as MutS-based, resolvase-based, ErrASE-based and the like. Exemplary methods include those described in Can et al., *Nucl. Acids Res.*, 32(20):e162 (2004) and Saaem et al., *Nucl. Acids Res., doi:* 10.1093/nar/gkr887 (2011) each of which are hereby incorporated by reference in their entireties.

In various embodiments, the methods disclosed herein comprise amplification of nucleic acids including, for example, oligonucleotides, subassemblies and/or polynucleotide constructs (e.g., nucleic acid sequences of interest). Amplification may be carried out at one or more stages during an assembly scheme and/or may be carried out one or more times at a given stage during assembly. Amplification methods may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391,544, 6,365,375, 6,294,323, 6,261,797, 6,124,090 and 5,612,199, or any other nucleic acid amplification method using techniques well known to those of skill in the art. In exemplary embodiments, the methods disclosed herein utilize PCR amplification.

In certain exemplary embodiments, methods for amplifying nucleic acid sequences are provided. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683, 195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277: 7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach* and *PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research*, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.,* 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., *Biotechniques,* 26:112-126 (1999); Becker-Andre et al., *Nucleic Acids Research,* 17:9437-9447 (1989); Zimmerman et al., *Biotechniques,* 21:268-279 (1996); Diviacco et al., *Gene,* 122:3013-3020 (1992); Becker-Andre et al., *Nucleic Acids Research,* 17:9437-9446 (1989); and the like.

In certain embodiments, methods of determining the sequence of one or more nucleic acid sequences of interest are provided. Determination of the sequence of a nucleic acid sequence of interest can be performed using a variety of sequencing methods known in the art including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al (2007) *Nat. Methods* 4:931), polymerized colony (POLONY) sequencing (U.S. Pat. Nos. 6,432,360, 6,485,944 and 6,511,803, and PCT/US05/06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., on cyclic array sequencing using platforms such as Roche 454, Illumina Solexa, AB-SOLiD, Helicos, Polonator platforms and the like, can also be utilized. High-throughput sequencing methods are described in U.S. Ser. No. 61/162,913, filed Mar. 24, 2009. A variety of light-based sequencing technologies are known in the art (Landegren et al. (1998) *Genome Res.* 8:769-76; Kwok (2000) *Pharmocogenomics* 1:95-100; and Shi (2001) *Clin. Chem.* 47:164-172).

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures tables and accompanying claims.

Example I

Assembly of Nucleic Acid Sequences in Emulsions Using a Column-Synthesized Barcode Library and Synthesis Library 3,000 orthogonal primer pairs were designed by beginning with a set of 240,000 orthogonal barcodes. From the set of 240,000, primers containing restriction enzyme recognitions sites to the following enzymes were removed: AatII, BsaI, BsmBI, SapI, BsrDI, BtsI, EarI, BspQI, BbsI, BspMI, BfuAI, NmeAIII, BamHI, NotI, EcoRI, KpnI, HindIII, XbaI, SpeI, PstI, PacI, and SbfI. Then, all primers with melting temperature below 60° C. and above 64° C. were removed to facilitate melting temperature matching of forward and reverse primers. Finally, an algorithm was implemented that screens primers for primer dimer formation that follows the AutoDimer program (Vallone and Butler (2004) *BioTechniques* 37:226), though giving double weight to the terminal 10 bases on the 3' end. All primers with a score greater than 3 were removed. After these screens, 155,608 primers remained. A BLAST library was constructed of all synthesized genes on the chip (except the fluorescent proteins), each oligonucleotide was screened against the library using BLAT (tileSize=6, stepSize=1, minMatch=2, maxGap=4), and any primers with hits were removed leaving 70,498 primers. A second BLAST library was constructed from the remaining primers, and a network elimination algorithm as described in Xu et al., *PNAS* 106(7):2289-2294 (2009) hereby incorporated by reference in its entirety was applied (tileSize=6, stepSize=1, –minMatch=1, maxGap=4) (see Li and Elledge (2007) *Nat. Methods* 4:251). This resulted in 8275 remaining primers, which were screened for formation of secondary structure (ΔG greater than −2). Finally, the 7738 remaining primers were aligned using clustalw2 (default options for DNA (slow)), clustered, and a phylogenetic tree was generated. This tree was traversed to find 200 nodes that were distant from one another and contained at least 30 primers each. Then, one primer from each batch was chosen. Primers were sorted on melting temperature, and then paired provided that they pass a primer dimer test (filtered dimers with a score greater than 4). The final output was a set of 3,000 pairs of orthogonal primers, grouped in sets of 100.

Four 20 nucleotide orthogonal barcodes shown below were chosen from the set of 3,000. These sequences were pre-pended with a 15 nt sequence used for quality control while optimizing reaction conditions. The common 15 nt sequence was ATGGACGCGTGGAGT (SEQ ID NO:1). The following barcode sequences were synthesized with 5' dual biotin linker by a commercial vendor (Integrated DNA Technologies) with the following sequences.

```
yaaA-bc
                                          (SEQ ID NO: 2)
ATGGACGCGTGGAGTGGGTGGGTAAATGGTAATGC yaaJ-bc
                                          (SEQ ID NO: 3)
ATGGACGCGTGGAGTTCCGACGGGGAGTATATACT talB-bc
                                          (SEQ ID NO: 4)
ATGGACGCGTGGAGTCATGTTTAGGAACGCTACCG mog-bc
                                          (SEQ ID NO: 5)
ATGGACGCGTGGAGTGTACATGAAACGATGGACGG
```

The following target nucleic acid sequences were chosen from natural genes in the *E. coli* genome: yaaA, yaaJ, talB, and mog encoding 282, 277, 290, and 280 nucleotides respectively.

```
>yaaA
                                          (SEQ ID NO: 6)
ATGCTGATTCTTATTTCACCTGCGAAAACGCTTGATTACCAAAGCCC

GTTGACCACCACGCGCTATACGCTGCCGGAGCTGTTAGACAATTCCC

AGCAGTTGATCCATGAGGCGCGGAAACTGACGCCTCCGCAGATTAGC

ACGCTGATGCGCATCAGCGACAAACTGGCGGGTATCAACGCCGCTCG

CTTTCATGACTGGCAGCCAGATTTCACGCCGGCGAATGCCCGCCAGG

CGATTCTGGCGTTTAAAGGTGATGTCTACACCGGCTTGCAGGCCGAA

>yaaJ
                                          (SEQ ID NO: 7)
ATGCCAGATTTTTTCTCCTTCATTAACAGCGTCCTTTGGGGATCGGT

AATGATTTACCTGCTCTTCGGCGCAGGTTGTTGGTTCACTTTTCGCA

CCGGATTTGTGCAGTTTCGCTACATCCGCCAGTTTGGCAAAAGTCTT

AAAAATAGCATTCATCCACAGCCAGGCGGTTTAACCTCATTTCAGTC

ATTGTGTACCAGTCTTGCGGCGCGCGTGGGTAGCGGCAACCTGGCCG

GCGTTGCGCTGGCTATTACCGCCGGTGGACCTGGAGCCGTCT

>talB
                                          (SEQ ID NO: 8)
ATGACGGACAAATTGACCTCCCTTCGTCAGTACACCACCGTAGTGGC

CGACACTGGGGACATCGCGGCAATGAAGCTGTATCAACCGCAGGATG

CCACAACCAACCCTTCTCTCATTCTTAACGCAGCGCAGATTCCGGAA

TACCGTAAGTTGATTGATGATGCTGTCGCCTGGGCGAAACAGCAGAG

CAACGATCGCGCGCAGCAGATCGTGGACGCGACCGACAAACTGGCAG

TAAATATTGGTCTGGAAATCCTGAAACTGGTTCCGGGCCGTATCTCA

ACTGAAGT

>mog
                                          (SEQ ID NO: 9)
ATGAATACTTTACGTATTGGCTTAGTTTCCATCTCTGATCGCGCATC

CAGCGGCGTTTATCAGGATAAAGGCATCCCTGCGCTGGAAGAATGGC

TGACATCGGCGCTAACCACGCCGTTTGAACTGGAAACCCGCTTAATC

CCCGATGAGCAGGCGATCATCGAGCAAACGTTGTGTGAGCTGGTGGA

TGAAATGAGTTGCCATCTGGTGCTCACCACGGGCGGAACTGGCCCGG

CGCGTCGTGACGTAACGCCCGATGCGACGCTGGCAGTAGCGGACC
```

Each gene was flanked by 15 nt sequences to facilitate PCR assembly within the emulsion with the following 15 nt primers.

```
ampfwd
                                         (SEQ ID NO: 10)
ACTCGACGGCCTCTG amprev
                                         (SEQ ID NO: 11)
ACACGCGCGTTGAAG
```

The four genes were then computationally processed into three overlapping oligonucleotide sequences. The overlaps were computationally optimized to have low secondary structure, melting temperatures of about 60° C., and about 20 nt according to design algorithms. The 5' end of each payload oligonucleotide sequence was prepended with the appropriate barcode sequence and the BtsI TypeIIs restriction enzyme recognition sequence (GCAGTG).

Automated algorithms were written to split constructs into oligonucleotide segments with partial overlaps to allow for stringent PCR assembly. Given a desired overlap size, allowable leeway on the size and position of the overlaps, and a melting temperature range, and Type IIs restriction enzyme site, the program automates the process of turning full-length gene constructs into oligonucleotides to be synthesized on the OLS platform. Briefly, the algorithm starts by padding the sequence with the proper construction primers. Then, the construct is evenly divided among the number of necessary oligonucleotides to construct the whole sequence, automatically determining the starting overlap positions. These overlap positions are screened for melting temperature falling within the defined length range, secondary structure formation (($\Delta G$ greater than −3), and self dimer formation (score greater than 3) to produce orthogonal primers. If these conditions are not met, the overlap lengths and positions are progressively varied and rechecked according to the predefined boundaries set at the beginning of the run. Once an overlap set is found that satisfies all the conditions, the final oligonucleotides are defined, and then flanked with the proper Type IIs restriction sites followed by the assembly-specific and plate-specific primer sequences. All sequences are rechecked for proper restriction enzyme cutting to make sure additional restriction sites were not added by adding primer sequences (in which case, the program pads with arbitrary sequence to remove the restriction site).

The reverse complement of the resultant oligonucleotide sequences were synthesized by Integrated DNA Technologies.

| | |
|---|---|
| yaaA-L | TCAACTGCTGGGAATTGTCTAACAGCTCCGGCAGC GTATAGCGCGTGGTGGTCAACGGGCTTTGGTAATC AAGCGTTTTCGCAGGTGAAATAAGAATCAGCATCA GAGGCCGTCGAGTCACTGCGCATTACCATTTACCC ACCC (SEQ ID NO: 12) |
| yaaJ-L | CAAATCCGGTGCGAAAAGTGAACCAACAACCTGCG CCGAAGAGCAGGTAAATCATTACCGATCCCCAAAG GACGCTGTTAATGAAGGAGAAAAAATCTGGCATCA GAGGCCGTCGAGTCACTGCAGTATATACTCCCCGT CGGA (SEQ ID NO: 13) |
| talB-L | TGGTTGTGGCATCCTGCGGTTGATACAGCTTCATT GCCGCGATGTCCCCAGTGTCGGCCACTACGGTGGT GTACTGACGAAGGGAGGTCAATTTGTCCGTCATCA GAGGCCGTCGAGTCACTGCCGGTAGCGTTCCTAAA CATG (SEQ ID NO: 14) |
| mog-L | CCGATGTCAGCCATTCTTCCAGCGCAGGGATGCCT TTATCCTGATAAACGCCGCTGGATGCGCGATCAGA GATGGAAACTAAGCCAATACGTAAAGTATTCATCA GAGGCCGTCGAGTCACTGCCCGTCCATCGTTTCAT GTAC (SEQ ID NO: 15) |
| yaaA-M | TCATGAAAGCGAGCGGCGTTGATACCCGCCAGTTT GTCGCTGATGCGCATCAGCGTGCTAATCTGCGGAG GCGTCAGTTTCCGCGCCTCATGGATCAACTGCTGG GAATTGTCTAACACACTGCGCATTACCATTTACCC ACCC (SEQ ID NO: 16) |
| yaaJ-M | TGGTACACAATGACTGAAATGAGGTTAAACCGCCT GGCTGTGGATGAATGCTATTTTTAAGACTTTTGCC AAACTGGCGGATGTAGCGAAACTGCACAAATCCGG TGCGAAAAGTGAACACTGCAGTATATACTCCCCGT CGGA (SEQ ID NO: 17) |
| talB-M | TGCGCGCGATCGTTGCTCTGCTGTTTCGCCCAGGC GACAGCATCATCAATCAACTTACGGTATTCCGGAA TCTGCGCTGCGTTAAGAATGAGAGAAGGGTTGGTT GTGGCATCCTGCGCACTGCCGGTAGCGTTCCTAAA CATG (SEQ ID NO: 18) |
| mog-M | CAACTCATTTCATCCACCAGCTCACACAACGTTTG CTCGATGATCGCCTGCTCATCGGGGATTAAGCGGG TTTCCAGTTCAAACGGCGTGGTTAGCGCCGATGTC AGCCATTCTTCCACACTGCCCGTCCATCGTTTCAT GTAC (SEQ ID NO: 19) |
| yaaA-R | ACACGCGCGTTGAAGTTCGGCCTGCAAGCCGGTGT AGACATCACCTTTAAACGCCAGAATCGCCTGGCGG GCATTCGCCGGCGTGAAATCTGGCTGCCAGTCATG AAAGCGAGCGGCGCACTGCGCATTACCATTTACCC ACCC (SEQ ID NO: 20) |
| yaaJ-R | ACACGCGCGTTGAAGAGACGGCTCCAGGTCCACCG GCGGTAATAGCCAGCGCAACGCCGGCCAGGTTGCC GCTACCCACGCGCGCCGCAAGACTGGTACACAATG ACTGAAATGAGGTCACTGCAGTATATACTCCCCGT CGGA (SEQ ID NO: 21) |
| talB-R | ACACGCGCGTTGAAGACTTCAGTTGAGATACGGCC CGGAACCAGTTTCAGGATTTCCAGACCAATATTTA CTGCCAGTTTGTCGGTCGCGTCCACGATCTGCTGC GCGCGATCGTTGCCACTGCCGGTAGCGTTCCTAAA CATG (SEQ ID NO: 22) |
| mog-R | ACACGCGCGTTGAAGGGTCCGCTACTGCCAGCGTC GCATCGGGCGTTACGTCACGACGCGCCGGGCCAGT TCCGCCCGTGGTGAGCACCAGATGGCAACTCATTT CATCCACCAGCTCCACTGCCCGTCCATCGTTTCAT GTAC (SEQ ID NO: 23) |

Barcoded beads were created as follows. 500 uL of Invitrogen Dynabeads M-270 Streptavidin were washed once and resuspended in 1 mL 2× Binding and Wash Buffer (10 mM Tris-HCl (pH 7.5), 1 mM EDTA, 2 M NaCl) using a magnetic separator. Four aliquots of 250 uL of bead suspension (i.e., 1.25 mg or 250 pmol binding capacity) was placed in a tube, and a different 500 pmol aliquot of dual-biotinylated barcode primer was added to each tube. The mixture was placed on rotator at room temperature for 15 minutes, washed in 2× Binding and Wash buffer, and resuspended in 500 uL 2× Binding and Wash Buffer.

The assembly oligonucleotides were attached to the barcoded beads as follows. 20 uL of each barcoded bead (80 uL volume total) was washed and resuspended in 50 uL 2× Binding and Wash buffer. 20 uL of a mixture of 2 uM each of 12 assembly oligonucleotides and 30 uL of PCR-grade water was added to bring the total volume to 100 uL. The mixture was placed in a thermal cycler with the following protocol:

5 m at 70° C.
Decrease to 50° C. by 0.1 C/s and hold for 1 min
Decrease to 40° C. by 0.1 C/s and hold for 1 min
Decrease to 15° C. by 0.1 C/s and hold forever The primers were extended as follows. The beads were washed and resuspended in 100 uL of 1× Binding and Wash Buffer to remove unbound assembly primers. Then 2 uL 120 U/uL Bst Polymerase Large Fragment (240 U, NEB), 1 uL *E. coli* SSB (5 ug, NEB), 2 uL 10× ThermoPol Buffer, and finally 15 uL H20 was added to the bead suspension. The mixture was incubated for 10 minutes with rotation. The mixture was then heated to 50° C. in a Eppendorf Thermomixer while shaking 2.0 uL of 25 mM dNTPs were added. The mixture was incubated for 20 minutes, brought to 55° C. for 10 minutes, and then at 65° C. for 60 minutes. The reaction was quenched with 10 uL 0.5M EDTA (25 mM EDTA).

Figure 2:
FIG. 2 is an imaged gel separation.

To characterize the effectiveness of the primer extension, beads from primer extension were washed twice in 0.1M NaOH to wash away annealed synthesis primers. Beads were then washed once with nuclease free water, and resuspended in 10 uL nuclease free water. The beads were heated to 80° C. for 2 min, and the tube was put onto the magnet and the supernatant was quickly removed to facilitate biotin removal from the bead. 5 uL of the supernatant was mixed with 5 uL Invitrogen 2×TBE Urea Sample buffer. Ladder (Invitrogen Quantitative Low Molecular Weight) and samples were prepared according to Novex 10% TBE-Urea Gels protocol and were subsequently loaded to a 10% TBE-Urea gel, and subsequently imaged using the Typhoon laser scanner (GE Healthcare). As shown in FIG. 2, the gel displayed correctly extended ~160 nt band (lane 2), slightly above the 150 nt ladder band (lane 1).

Since Bst polymerase generates 3' adenine overhangs, T4 DNA polymerase was used to correct the overhang on the primer extended beads before further processing using the conditions below. The mixture was incubated for 15 min @ 12° C. Then 10 uL 0.5M EDTA was added to the reaction mixture to quench, followed by a 20 min heat inactivation at 75° C.

400 uL beads in T.E.
    50 uL 3 U/uL T4 DNA Polymerase
    5 uL 25 mM dNTP
    50 uL 10×NEB Buffer 2

The ability of BtsI to digest close to the bead surface within the PCR buffer was tested as follows. A 60 uL reaction volume of the following was prepared.

30 uL primer extended beads
    12 uL Buffer A (Kapa Biosystems)
    12 uL KAPA Enhancer (Kapa Biosystems)
    0.5 uL BSA (10 ug/uL) (NEB)
    4.5 uL Bts I (10 U/uL) (NEB)
    1 uL 25 mM dNTP (NEB)

Figure 3:
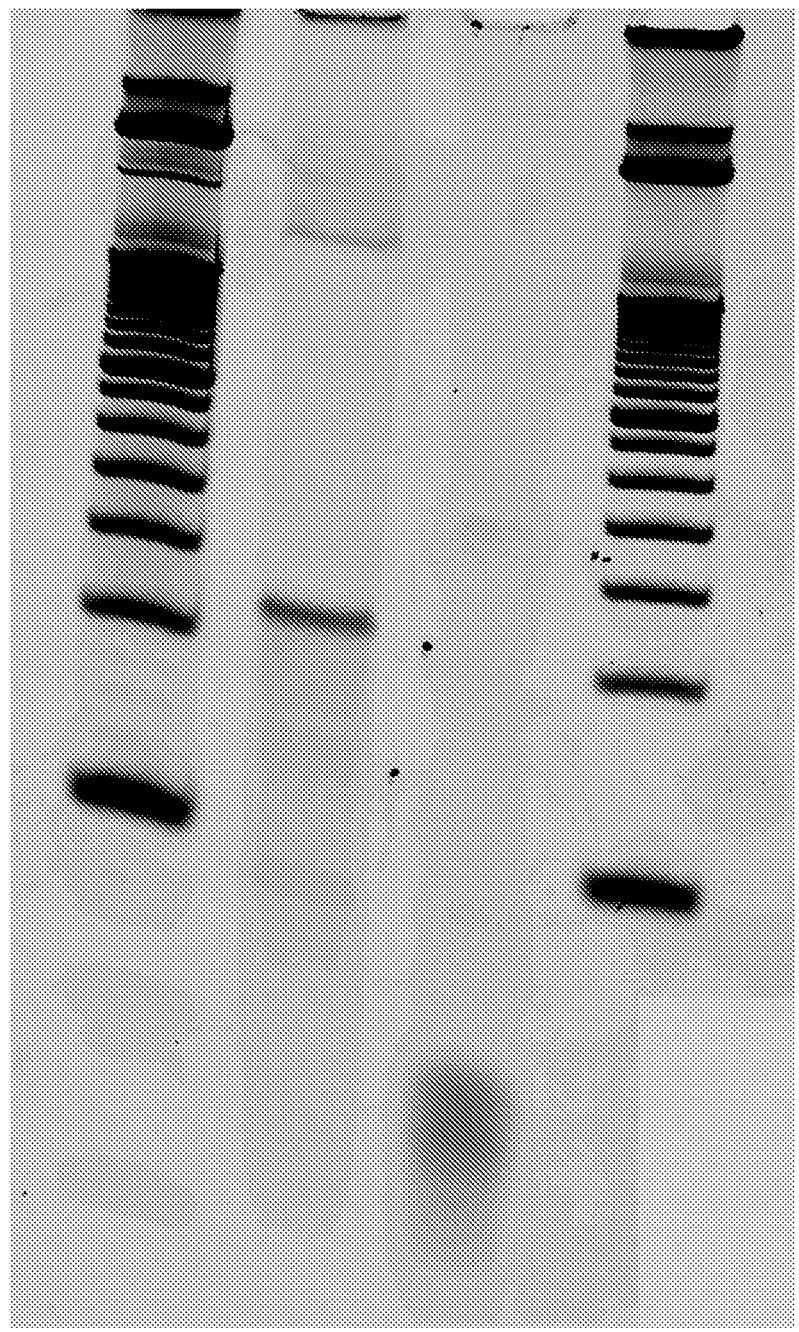
FIG. 3 is an imaged gel separation.

The reaction mixture was incubated at 55° C. for 1.5 hours. The beads were washed and the supernatant was collected to collect digested product from beads. In addition, to collect the bead-bound fraction, the beads were washed and re-suspended in 10 uL nuclease-free water. The beads were then heated to 80° C. for 2 min, followed by immediate collection of the supernatant as above. Both the digested supernatant and bead-bound component were loaded onto 10% TBE-Urea gel following the sample preparation protocols provided by Invitrogen. Lanes 1 and 4 in the gel of FIG. 3 are 50 bp ladder (Invitrogen). Lane 2 shows the supernatant, which indicates correctly digested 130 nt product, while the bead bound fraction only retains the processed barcode sequence.

Emulsion assembly of target nucleic acids using the extended beads were carried out with KAPA Robust Enhancer added (Condition A) and without KAPA Robust Enhancer added (Condition B).

Condition A 101 uL total volume:
    40 uL primer extended beads
    20 uL Buffer A (Kapa Biosystems)
    20 uL Enhancer (Kapa Biosystems)
    10 uL KAPA Robust Hotstart Polymerase (Kapa Biosystems)
    7 uL BtsI (10 U/uL, NEB)
    1 uL BSA (10 ug/uL, NEB)
    2 uL 25 mM dNTP (NEB)
    0.5 uL 100 uM Ampfwd primer
    0.5 uL 100 uM Amprev primer
    Condition B (101 uL total volume):
    40 uL primer extended beads
    40 uL Buffer A (Kapa Biosystems)
    10 uL KAPA Robust Hotstart Polymerase (Kapa Biosystems)
    7 uL BtsI (10 U/uL, NEB)
    1 uL BSA (10 ug/uL, NEB)
    2 uL 25 mM dNTP (NEB)
    0.5 uL 100 uM Ampfwd primer
    0.5 uL 100 uM Amprev primer The oil component of the water-in-oil emulsion was prepared by mixing 4.4 ml Tegosoft, 1.2 ml mineral oil and 425 uL ABIL WE09.

900 uL oil mixture was added to each of two 2 ml Ambion tube, and then 100 uL of each PCR mixture was placed at the bottom of the tubes. The tubes were put onto the foam vortex holder and was vortexed for 3 min at max speed in cold room at 4° C. The tubes were placed on ice for 5 min to de-bubble. A 1 mL pipette tip was used to transfer 100 uL emulsion aliquots into PCR tubes. The reactions were thermal cycled as follows.

1. 55° C. for 90 min
2. 94° C. for 2 min
3. 94° C. for 15 sec
4. 57° C. for 20 sec
5. 72° C. for 45 sec
6. Go to step 3 for additional 60 cycles
7. 72° C. for 5 min
8. 4° C. forever (i.e., store at 4° C. until sample is to be taken out)

The emulsion reactions were pooled together in a non-stick microcentrifuge tube (Ambion), and 1 ml isobutanol was added. About 400 uL to about 450 uL of the mixture was added to several 1.7 mL microcentrifuge tubes (Eppendorf). In each eppendorf tube, 400 uL PB (Qiagen PCR cleanup kit) was added to each tube, thoroughly vortexed, and spun down for two minutes at 16,000 g. The upper organic layer was removed and standard Qiagen PCR cleanup protocol was used, except that in the elution step, the contents were transferred to a fresh eppendorf tube to avoid any remaining oil component contamination.

Figure 4:
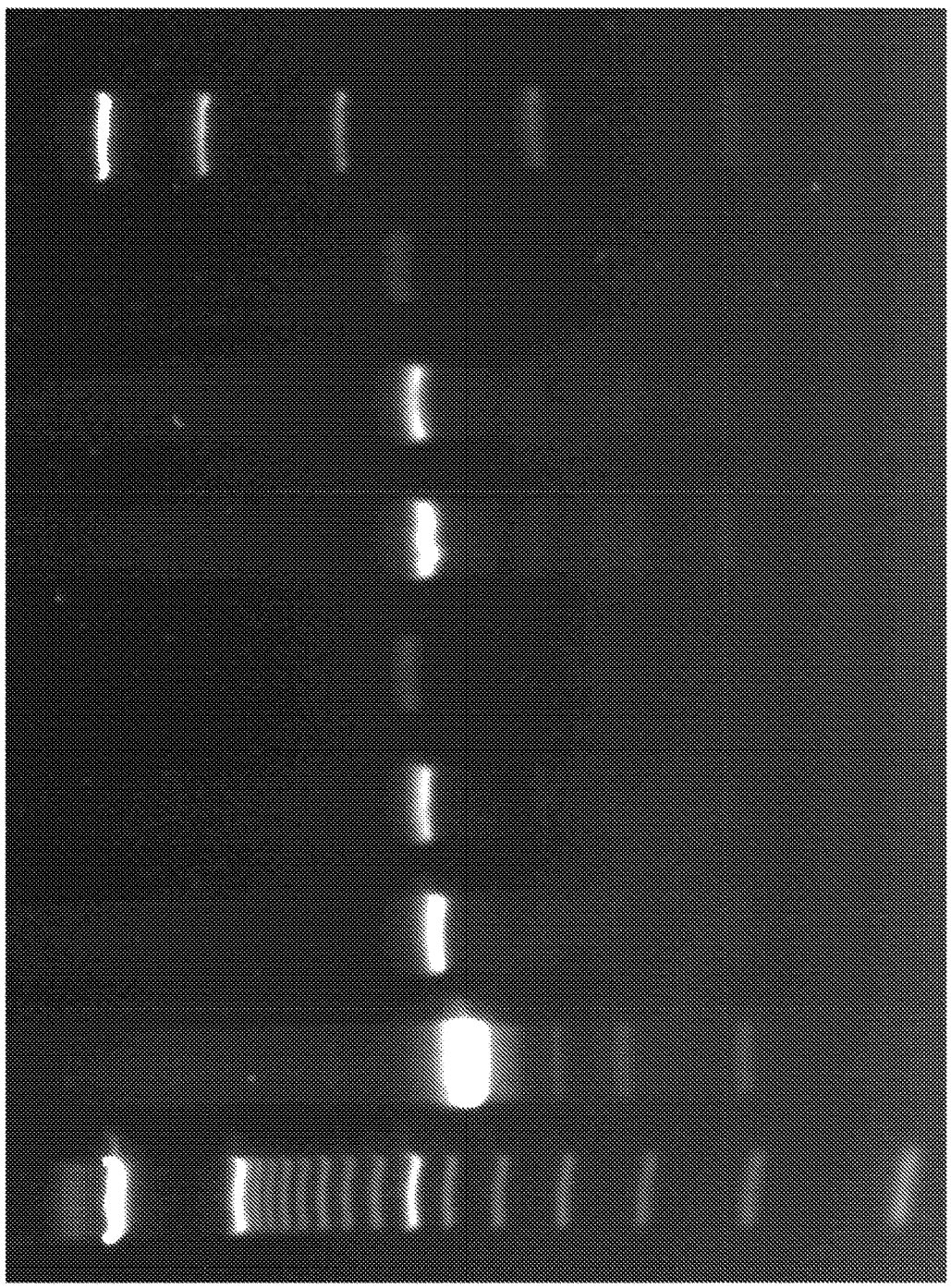
FIG. 4 is an imaged gel separation.

1, 0.5, and 0.1 uL of Condition B (Lanes 2, 3, and 4 respectively of FIG. 4) and Condition A (Lanes 5, 6, and 7 respectively of FIG. 4) were run with 50 bp Ladder and Low Range Quantitative Ladder (Invitrogen) lanes (Lanes 1 and 8 respectively of FIG. 4). The bands displayed correct ~310 bp band. Cloning, and subsequent Sanger sequencing of this band demonstrated all 4 constructs were successfully assembled in both conditions.

Example II

Assembly of Nucleic Acid Sequences in Emulsions Using a Chip-Synthesized Barcode Library and Synthesis Library From the 3,000 orthogonal primer pairs of Example I, 1,000 20 nucleotide orthogonal barcodes were chosen. A BtsI TypeIIs restriction enzyme recognition site was added 3' to the 20 nucleotide barcode, and subsequently was pre- and post-pended with 15 nt PCR primer sequences for amplication. The common 15 nt PCR primers were:

```
bc-amp-F
                            (SEQ ID NO: 24)
ATGGACGCGTGGAGT bc-amp-R
                            (SEQ ID NO: 25)
TAGGGCTCCGCTTGG
```

The 1000 barcode library was synthesized on a 12,000 feature chip from CustomArray.

1000 target nucleic acids were chosen from natural genes in the *E. coli* genome. For this test we chose 5' end of 1000 genes encoding ~280 bp. The actual length for each construct varied depending on the lengths of the designed overlaps between oligonucleotides. Each gene was flanked by 15 nt sequences to facilitate PCR assembly within the emulsion with the following 15 nt primers.

```
asmblyfwd
                              (SEQ ID NO: 26)
ACTCGACGGCCTCTG asmblyrev
                              (SEQ ID NO: 27)
ACACGCGCGTTGAAG
```

The 1000 genes were then computationally processed into three overlapping oligonucleotide sequences. The overlaps were computationally optimized using design algorithms to have low secondary structure, melting temperatures of about 60° C., and about 20 nt. Each oligo sequence was pre- and post-pended with the BtsI TypeIIs restriction enzyme recognition sequence (GCAGTG, or reverse complement). The 5' end of the each payload oligonucleotide sequence was prepended with the appropriate barcode sequence and the BtsI TypeIIs restriction enzyme recognition sequence (GCAGTG). Finally, the whole sequence was pre- and post-pended to allow amplification by the following primers:

```
chpampfwd
                              (SEQ ID NO: 28)
CGAGCCGTGGTTCCT chpamprev
                              (SEQ ID NO: 29)
CGCTGGGAGGGTGTT
```

The reverse complements of the resultant oligonucleotide sequences were synthesized by CustomArray on the same 12,000 feature chip as the barcode library.

A barcoded bead library was constructed as follows. Lyophilized oligonucleotide library from CustomArray was resuspended in 100 uL TE. 4 uL of this library was combined with 5 uL of a mixture of 10 uM each of bc-amp-F and bc-amp-R, 91 uL water, and 100 uL 2× Kapa Sybr Fast Master Mix (Kapa Biosystems). Amplifications were monitored on a Bio-Rad CFX Real-time Detection System, and stopped as exponential amplification phase came to an end. The reaction was purified using Qiagen Qiaquick PCR Purification Kit.

The amplified library was diluted 1:10,000 or 1:100,000 to a concentration of 1.4 pg/uL or 0.14 pg/uL respectively. 250 uL of Invitrogen M-270 were washed twice with 2× Binding and Wash Buffer. 50 uL of 100 uM bc-amp-F (dual biotin and 18C spacer on primer) was added to beads and incubated 15 minutes at 37° C. Beads were again washed twice in 250 uL of 2× Binding and Wash Buffer and resuspended in 40 uL Binding and Wash Buffer. Emulsion PCR conditions were set up as follows. The following liquid phase was used.
1. 20 uL Buffer A (Kapa Biosystems)
2. 20 uL Kapa Robust Enhancer (Kapa Biosystems)
3. 10 uL KAPA Robust enzyme (5 U/uL; Kapa Biosystems)
4. 5 uL BSA (10 ug/uL) (New England Biolabs)
5. 2 uL 25 mM dNTP (New England Biolabs)
6. 2 uL 10 uM Forward Primer (bc-amp-F: ATG GAC GCG TGG AGT) (SEQ ID NO:30)
7. 5 uL 100 uM Reverse Primer (bc-rev-BioT-R: /5BioTEG/ TAG GGC TCC GCT TGG) (SEQ ID NO:31)
8. 16 uL Nuclease Free Water (Ambion)
9. 10 uL diluted barcode primer
10. 10 uL beads concentrated from 40 uL beads from 3.5.

The oil phase was 4.4 mL Tegasoft, 1.2 mL mineral oil, and 425 uL ABIL WE09. 900 uL oil component was added to a 2 ml Ambion RNA-free tube, and then 130 uL PCR/bead mixture was added to the bottom of the tube. The mixture was vortexed for three minutes at max speed in the cold room. The sample was then left on ice for 5 min to de-bubble. 1 mL tips were used to split the emulsions into PCR strip tubes, and placed in a thermal cycler with the following program:
1. 94° C. for 2 min
2. 94° C. for 15 sec
3. 57° C. for 20 sec
4. 72° C. for 45 sec
5. Go to step 2 for additional 60 cycles
6. 72° C. for 5 min
7. 4° C. forever The emulsion mixture was pooled in a 2 mL tube, and 1200 uL of isopropanol was added and vortexed for 30 seconds to break the emulsion. The sample was centrifuged at 1500×g for 30 seconds. The sample was placed onto a magnet for 1 minute and the sample was removed. The isopropanol wash was repeated. The beads were then washed three times with 500 uL of NXS buffer (10 mM TrisHCl, pH 7.5, 1 mM EDTA (pH 8.0), 100 mM NaCl, 1% Triton X-100, 1% (w/v) SDS). Finally, beads were washed with 500 uL TK buffer (20 mM Tris-HCl pH 8.4 and 50 mM KCl) and transferred to a new 1.5 mL tube. Beads were resuspended in 50 uL of 1× Buffer 4 (NEB), 2 uL BtsI (NEB), and 0.5 uL BSA (NEB) and incubated for 45 minutes at 55° C., and then 15 minutes at 80° C. The beads were made single stranded by washing twice in 0.1N NaOH.

To amplify the library of 3,000 assembly oligonucleotides from the chip, single stranded DNA was prepared and the following conditions used.
1. 4 uL 130 mer chip condition 1 oligos
2. 5 uL primer working mix 10 uM concentration
3. skpp15-18-F: /5Phos/CGAGCCGTGGTTCCT (SEQ ID NO:32)
4. skpp15-18-R: C*G*CTGGGAGGGTGT/3deoxyU/ (SEQ ID NO:33)
5. 5Phos is used to promote Lambda exonuclease processevity
6. ~91 uL H2O
7. ~100 uL KAPA SYBR Fast The reaction was stopped when the amplification curve leveled. A Qiagen cleanup kit was used to clean up the real time PCR product, which was further used for a preparative PCR using the following components and PCR conditions.
1. 34.8 mL dH2O
2. 4 mL 10×PCR Buffer
3. 200 uL 100 uM Forward Primer: skpp15-18-F: /5Phos/ CGAGCCGTGGTTCCT (SEQ ID NO:34)
4. 200 uL 100 uM Reverse Primer: skpp15-18-R: C*G*CTGGGAGGGTGT/3deoxyU/(SEQ ID NO:35)
5. 320 uL 25 mM dNTP
6. 800 U (160 uL) Taq polymerase
7. 40 uL Template from cleaned up real-time PCR product
PCR Conditions
1. 94° C. for 180 sec
2. 94° C. for 10 sec 3. 62° C. for 60 sec
4. Go to step 2, 12 more times
5. 68° C. for 60 sec
6. 4° C. for ever Millipore MWCO 10K filter was used to cleanup the PCR products. The protocol provided by Millipore was followed. The final elute has a volume approximately ~320 uL with a concentration of 708.7 ng/uL. DNA was then digested with Lambda Exonuclease to make the PCR product single stranded. Briefly, 320 uL of DNA from previous step, 184.1 uL Lambda Exonuclease, and 55 uL Lambda Exonuclease 10× Buffer (Enyzmatics) was incubated at 37° C. for 1 hour, and then 75° C. for 15 minutes. Reaction was again run through a Millipore MWCO 10K filter to wash.

Multiplexed primer extension was carried out as follows. 45 uL of the assembly oligonucleotide library and 50 ul of the barcode bead library in 2× Binding and Wash Buffer were incubated as follows:
1. 5 min @ 70° C.
2. Decrease to 50° C. by 0.1° C./s and hold for 1 min
3. Decrease to 40° C. by 0.1° C./s and hold for 1 min
4. Decrease to 15° C. by 0.1 C/s and hold for ever Beads were then washed and resuspended in 100 uL 1× Binding and Wash buffer. Primer extension was then attempted by resuspending beads in 20 uL of 1× ThermoPol Buffer (NEB), 2 uL of 120 U/uL Bst Polymerase (NEB), 1 uL E. coli SSB (5 ug, NEB), 2 uL 10× ThermoPol Buffer (NEB), and 13 uL water. The mixture was incubated and rotated for 10 minutes at room temperature. The mixture was then heated to 50° C. in an Eppendorf Thermomixer while shaking at 700 rpm. 2.0 uL of 25 mM dNTPs were added and then incubated for 20 minutes, brought to 55° C. for 10 minutes, and then 65° C. for 1 hour. The reaction was quenched with 10 uL 0.5M EDTA. The beads were washed three times in 1× Binding and Wash Buffer and eluted into 45 uL TE Buffer.

Nucleic acids were assembled in emulsion droplets as follows. 40 uL of beads from previous step are mixed with 20 uL Buffer A (Kapa Biosystems), 20 uL Robust Enhancer (Kapa Biosystems), 10 uL KAPA Robust Hotstart, 7 uL BtsI, 1 uL BSA, 2 uL dNTP, 0.5 uL 100 uM asmblyfwd primer, and 2 uL 100 uM asmblyrev primer. Emulsions are prepared as before and run under the following conditions:
1. 55° C. for 90 min (to facilitate BtsI restriction digest)
2. 94° C. for 2 min (to activate hotstart polymerase)
3. 94° C. for 15 sec
4. 57° C. for 20 sec
5. 72° C. for 45 sec
6. Go to step 3 for additional 60 cycles
7. 72° C. for 5 min
8. 4° C. forever After emulsion, the mixture is pooled together, and 1 mL isobutanol is added. Reactions were split into several Eppendorf tubes with 450 uL each, and 400 uL Buffer PB (Qiagen) was added to each tube, thoroughly vortexed, and spun for 2 minutes at 16,000×g. The upper organic layer was removed, and continued with the normal Qiagen cleanup protocol. For each column, 30 uL EB was eluted and run in 3 different dilutions shown below in FIG. 5, where a correct ~300 bp band was present.

Figure 6:
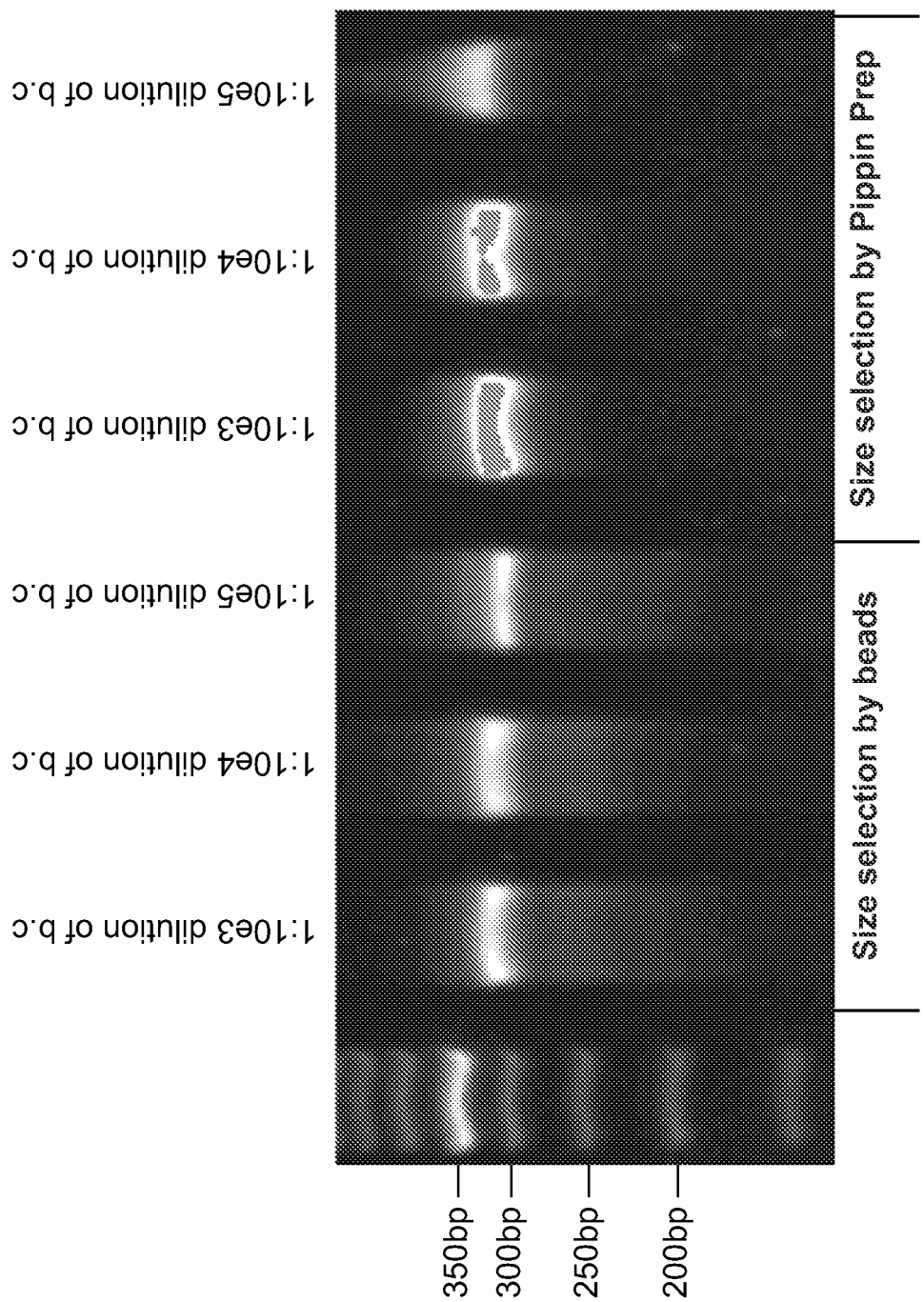
FIG. 6 is an imaged gel separation.

As shown in FIG. 6, the 300 bp band was purified by either using Pippen Prep (Sage Science) or bead-based purification, and reamplified by real-time PCR for 13 cycles as before.

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference herein in their entirety for all purposes to the same extent as if each individual publication or patent application were specifically indicated to be so incorporated by reference.

---

What is claimed is:

1. A method of synthesizing a target nucleic acid sequence comprising the steps of:
   localizing a plurality of oligonucleotide subsequences defining an oligonucleotide set corresponding to a particular target nucleic acid sequence by hybridization to a predesigned sequence attached to a bead that is unique to each oligonucleotide set;
   placing the bead within an emulsion droplet;
   separating the plurality of oligonucleotide subsequences from the bead such that the plurality of oligonucleotide subsequences remain within the emulsion droplet; and
   assembling within the emulsion droplet the plurality of oligonucleotide subsequences to form the target nucleic acid sequence.

2. The method of claim 1 wherein the target nucleic acid sequence includes at least 300 nucleotides.

3. The method of claim 1 wherein the target nucleic acid sequence includes at least 1,000 nucleotides.

4. The method of claim 1, wherein the target nucleic acid sequence includes at least 2,500 nucleotides.

5. The method of claim 1, wherein the target nucleic acid sequence includes at least 5,000 nucleotides.

6. The method of claim 1, wherein the target nucleic acid sequence is a DNA sequence.

7. The method of claim 6, wherein the DNA sequence is a regulatory element, a gene, a pathway or a genome.

8. The method of claim 1 further comprising obtaining the target nucleic acid.

9. A method of synthesizing a plurality of target nucleic acid sequences comprising the steps of:
 for each target nucleic acid sequence within the plurality, localizing a plurality of oligonucleotide subsequences defining an oligonucleotide set corresponding to a particular target nucleic acid sequence by hybridization to a predesigned sequence attached to a bead that is unique to the oligonucleotide set so as to create a plurality of beads with a plurality of oligonucleotide sets corresponding to the plurality of target nucleic acid sequences;
 placing the plurality of beads within a plurality of emulsion droplets;
 separating the plurality of oligonucleotide subsequences from a bead within an emulsion droplet;
 assembling within the emulsion droplet the plurality of oligonucleotide subsequences to form one of the plurality of target nucleic acid sequences.

10. The method of claim 9, wherein the plurality of oligonucleotide sets includes at least 50 oligonucleotide sets.

11. The method of claim 9, wherein the plurality of oligonucleotide sets includes at least 100 oligonucleotide sets.

12. The method of claim 9, wherein the plurality of oligonucleotide sets includes at least 500 oligonucleotide sets.

13. The method of claim 9, wherein the plurality of oligonucleotide sets includes at least 750 oligonucleotide sets.

14. The method of claim 9, wherein the plurality of oligonucleotide sets includes at least 1000 oligonucleotide sets.

15. The method of claim 9 wherein members of the plurality of target nucleic acid sequences include at least 500 nucleotides.

16. The method of claim 9 wherein members of the plurality of target nucleic acid sequences include at least 1,000 nucleotides.

17. The method of claim 9, wherein members of the plurality of the target nucleic acid sequences include at least 2,500 nucleotides.

18. The method of claim 9, wherein members of the plurality of the target nucleic acid sequences include at least 5,000 nucleotides.

19. The method of claim 9, wherein members of the plurality of the target nucleic acid sequences include DNA sequences.

20. The method of claim 19, wherein the DNA sequences are a regulatory element, a gene, a pathway or a genome.

21. The method of claim 9 further comprising obtaining the plurality of target nucleic acids.

22. A method of synthesizing a target nucleic acid sequence comprising the steps of:
 amplifying a plurality of oligonucleotide subsequences defining an oligonucleotide set corresponding to a particular target nucleic acid sequence by using orthogonal primers that hybridize to a pair of orthogonal primer binding sites that are unique to the oligonucleotide set;
 removing the orthogonal primer binding sites from the amplified plurality of oligonucleotide subsequences;
 attaching the amplified plurality of oligonucleotide subsequences to a bead;
 synthesizing a complementary strand to each of the amplified plurality of oligonucleotide subsequences to produce a plurality of double stranded nucleic acids;
 placing the bead within an emulsion droplet;
 separating the plurality of double stranded nucleic acids from the bead such that the plurality of double stranded nucleic acids remain within the emulsion droplet; and
 assembling within the emulsion droplet the plurality of double stranded nucleic acids to form the target nucleic acid sequence.

23. The method of claim 22 wherein the target nucleic acid sequence includes at least 500 nucleotides.

24. The method of claim 22 wherein the target nucleic acid sequence includes at least 1,000 nucleotides.

25. The method of claim 22, wherein the target nucleic acid sequence includes at least 2,500 nucleotides.

26. The method of claim 22, wherein the target nucleic acid sequence includes at least 5,000 nucleotides.

27. The method of claim 22, wherein the target nucleic acid sequence is a DNA sequence.

28. The method of claim 27, wherein the DNA sequence is a regulatory element, a gene, a pathway or a genome.

29. The method of claim 22 further comprising obtaining the target nucleic acid.

30. A method of synthesizing a plurality of target nucleic acid sequences comprising the steps of:
 amplifying a plurality of oligonucleotide subsequences defining a plurality of oligonucleotide sets with each oligonucleotide set corresponding to a particular target nucleic acid sequence by using orthogonal primers that hybridize to a pair of orthogonal primer binding site sequences that are unique to each oligonucleotide set;
 removing the orthogonal primer binding sites from the amplified plurality of oligonucleotide subsequences;
 for each oligonucleotide set, attaching corresponding amplified oligonucleotide subsequences defining the set to a bead;
 synthesizing a complementary strand to each of the amplified oligonucleotide subsequences to produce a plurality of double stranded nucleic acids;
 placing the bead within an emulsion droplet;
 separating the plurality of double stranded nucleic acids from the bead such that the plurality of double stranded nucleic acids remain within the emulsion droplet;
 assembling within the emulsion droplet the plurality of double stranded nucleic acids to form one of the plurality of target nucleic acid sequences.

31. The method of claim 30, wherein the plurality of oligonucleotide sets includes at least 50 oligonucleotide sets.

32. The method of claim 30, wherein the plurality of oligonucleotide sets includes at least 100 oligonucleotide sets.

33. The method of claim 30, wherein the plurality of oligonucleotide sets includes at least 500 oligonucleotide sets.

34. The method of claim 30, wherein the plurality of oligonucleotide sets includes at least 750 oligonucleotide sets.

35. The method of claim 30, wherein the plurality of oligonucleotide sets includes at least 1000 oligonucleotide sets.

36. The method of claim 30 wherein members of the plurality of target nucleic acid sequences include at least 500 nucleotides.

37. The method of claim 30 wherein members of the plurality of target nucleic acid sequences include at least 1,000 nucleotides.

38. The method of claim 30, wherein members of the plurality of the target nucleic acid sequences include at least 2,500 nucleotides.

39. The method of claim 30, wherein members of the plurality of the target nucleic acid sequences include at least 5,000 nucleotides.

40. The method of claim 30, wherein members of the plurality of the target nucleic acid sequences include DNA sequences.

41. The method of claim 40, wherein the DNA sequences are a regulatory element, a gene, a pathway or a genome.

42. The method of claim 30 further comprising obtaining the plurality of target nucleic acids.

\* \* \* \* \*